US010624750B2

(12) United States Patent
Castro et al.

(10) Patent No.: US 10,624,750 B2
(45) Date of Patent: Apr. 21, 2020

(54) THREE-DIMENSIONALLY PRINTED TISSUE ENGINEERING SCAFFOLDS FOR TISSUE REGENERATION

(71) Applicant: Nanochon, LLC, Burke, VA (US)

(72) Inventors: Nathan Jonathan Castro, El Paso, TX (US); Benjamin Blair Holmes, Washington, DC (US)

(73) Assignee: NANOCHON, LLC, Burke, VA (US)

( * ) Notice: Subject to any disclaimer, the term of this patent is extended or adjusted under 35 U.S.C. 154(b) by 14 days.

(21) Appl. No.: 15/671,048

(22) Filed: Aug. 7, 2017

(65) Prior Publication Data

US 2018/0055643 A1 Mar. 1, 2018

Related U.S. Application Data

(60) Provisional application No. 62/371,805, filed on Aug. 7, 2016.

(51) Int. Cl.
*A61F 2/30* (2006.01)
*A61L 27/54* (2006.01)
(Continued)

(52) U.S. Cl.
CPC ...... *A61F 2/30942* (2013.01); *A61F 2/30771* (2013.01); *A61L 27/12* (2013.01); *A61L 27/18* (2013.01); *A61L 27/48* (2013.01); *A61L 27/54* (2013.01); *A61L 27/56* (2013.01); *A61L 27/58* (2013.01); *B29C 64/30* (2017.08); *B33Y 10/00* (2014.12); *B33Y 80/00* (2014.12); *C08J 9/26* (2013.01); *A61F 2002/2835* (2013.01); *A61F 2002/3084* (2013.01); *A61F 2002/3092* (2013.01); *A61F 2002/3093* (2013.01);
(Continued)

(58) Field of Classification Search
CPC ....................................................... A61F 2/30
See application file for complete search history.

(56) References Cited

U.S. PATENT DOCUMENTS 8,796,015 B2    8/2014   Gingras
2008/0124766 A1  5/2008   Kuboki et al.
(Continued)

FOREIGN PATENT DOCUMENTS

DE     102013011243 A1    1/2015

OTHER PUBLICATIONS

Aski, et al. The Microfracture Technique for the Treatment of Full-Thickness Articular Cartilage Lesions of the Knee: Midterm Results. Arthroscopy: The Journal of Arthroscopic and Related Surgery, 24.11 (2008): 1214-1220.
(Continued)

*Primary Examiner* — Yashita Sharma
(74) *Attorney, Agent, or Firm* — Wilson Sonsini Goodrich & Rosati, PC

(57) ABSTRACT

The present disclosure relates to a three-dimensionally (3D) printed tissue engineering scaffold for tissue regeneration and a method for manufacturing the 3D printed tissue engineering scaffold. The 3D printed tissue engineering scaffold may be fabricated at least in part from a composite material having an insoluble component and soluble component. The three-dimensional tissue scaffolds of the disclosure may be fabricated via a rapid prototyping machine. In some instances, the three-dimensional shape of the fabricated tissue engineering scaffold may correspond to a three-dimensional shape of a tissue defect of a patient.

18 Claims, 21 Drawing Sheets

(51) Int. Cl.
| | |
|---|---|
| A61L 27/58 | (2006.01) |
| A61L 27/48 | (2006.01) |
| B33Y 10/00 | (2015.01) |
| B33Y 80/00 | (2015.01) |
| B29C 64/30 | (2017.01) |
| A61L 27/12 | (2006.01) |
| A61L 27/18 | (2006.01) |
| A61L 27/56 | (2006.01) |
| C08J 9/26 | (2006.01) |
| B29C 64/118 | (2017.01) |
| A61F 2/28 | (2006.01) |
| B29K 71/00 | (2006.01) |
| B29K 75/00 | (2006.01) |
| B29L 31/00 | (2006.01) |
| C08J 9/00 | (2006.01) |

(52) U.S. Cl.
CPC .......... A61F 2002/3097 (2013.01); A61F 2002/30766 (2013.01); A61F 2002/30784 (2013.01); A61F 2002/30838 (2013.01); A61F 2002/30948 (2013.01); A61F 2002/30968 (2013.01); A61F 2002/30971 (2013.01); A61F 2002/30985 (2013.01); A61L 2400/08 (2013.01); A61L 2400/12 (2013.01); A61L 2430/02 (2013.01); A61L 2430/06 (2013.01); B29C 64/118 (2017.08); B29K 2071/02 (2013.01); B29K 2075/00 (2013.01); B29K 2995/0056 (2013.01); B29L 2031/7532 (2013.01); C08J 9/0061 (2013.01); C08J 9/0071 (2013.01); C08J 2201/0464 (2013.01); C08J 2205/04 (2013.01); C08J 2205/042 (2013.01); C08J 2205/044 (2013.01); C08J 2205/06 (2013.01); C08J 2207/10 (2013.01); C08J 2325/06 (2013.01); C08J 2367/04 (2013.01); C08J 2375/04 (2013.01); C08J 2405/04 (2013.01); C08J 2429/04 (2013.01); C08J 2471/02 (2013.01); C08J 2489/00 (2013.01)

(56) References Cited

U.S. PATENT DOCUMENTS

| | | |
|---|---|---|
| 2013/0172999 A1 | 7/2013 | Kaplan et al. |
| 2016/0067375 A1 | 3/2016 | Holmes et al. |

OTHER PUBLICATIONS

Bergmeister, et al. Biodegradable, thermoplastic polyurethane grafts for small diameter vascular replacements. Acta Biomaterialia 11 (2015): 104-113.
Bhat, et al. Supermacroprous chitosan-agarose-gelatin cryogels: in vitro characterization and in vivo assessment for cartilage tissue engineering. J. R. Soc. Interface 8 (2011): 540-554.
Bianchi, et al. Formation of Hyaline Cartilage Tissue by Passaged Human Osteoarthritic Chondrocytes. Tissue Engineering: Part A 23.3 (2017): 156-166.
Boone, et al. Bone attachment to hydoxyapatite coated polymers. J. Biomed. Mater. Res.: Applied Biomaterials, 23.A2 (1989): 183-199.
Broom, et al. Dynamic fracture characteristics of the osteochondral junction undergoing shear deformation. Med. Eng. Phys. vol. 18, No. 5, (1996): 396-404.
Castro, et al. Biomimetic Biphasic 3-D Nanocomposite Scaffold for Osteochondral Regeneration. Aiche journal 60, (2014) 432-442.
Castro, et al. Design of a Novel 3D Printed Bioactive Nanocomposite Scaffold for Improved Osteochondral Regeneration. Cell Mol Bioeng. 8.3 (2015): 416-432.
Castro, et al. Integrating Biologically Inspired Nanomaterials and Table-top Stereolithography for 3D Printed Biomimetic Osteochondral Scaffolds. Nanoscale.7.33 (2015): 14010-14022.
Castro, et al. Simulated Body Fluid Nucleation of Three-Dimensional Printed Elastomeric Scaffolds for Enhanced Osteogenesis. Tissue Engineering: Part A 22.13 and 14 (2016): 940-948.
Celik, et al. Histologic Analysis of Prefabricated, Vascularized Bone Grafts: An Experimental Study in Rabbits. J Oral Maxillofac Surg 58 (2000): 292-296.
Chen, et al. Repair of articular cartilage defects: part II. Treatment options. Am J Orthop 28:2 (1999): 88-96.
Chung, et al. Rapid and Low-cost Prototyping of Medical Devices Using 3D Printed Molds for Liquid Injection Molding. J. Vis. Exp. 88 (2014): e51745.
Cui, et al. Biologically Inspired Smart Release System Based on 3D Bioprinted Perfused Scaffold for Vascularized Tissue Regeneration. Adv. Sci. 3 (2016): 1600058.
Czitrom, et al. Bone Banking in Community Hospitals. Bone Transplantation. Berlin. Heidelberg: Springer, 1989: 151-154.
Dong, et al. Degradation and biocompatibility of porous nano-hydroxyapatite/polyurethane composite scaffold for bone tissue engineering. Applied Surface Science 255 (2009): 6087-6091.
Erggelet, et al. Autologous chondrocyte implantation versus ACI using 3D-bioresorbable graft for the treatment of large full-thickness cartilage lesions of the knee. Arch Orthop Trauma Surg (2010): 130: 957-964.
Fierz, et al. The morphology of anisotropic 3D-printed hydroxyapatite scaffolds. Biomaterials 29 (2008): 3799-3806.
Gill, et al. The Prefabrication of a Bone Graft in a Rat Model. Journal of Hand Surgery, vol. 23A, No. 2 (1998): 312-321.
Goldberg, et al. Biological resurfacing: an alternative to total joint arthroplasty. Orthopedics vol. 17, No. 9 (1994): 819-821.
Habibovic, et al. Osteoconduction and osteoinduction of low-temperature 3D printed bioceramic implants. Biomaterials 29 (2008): 944-953.
Holmes, et al. Development of Novel Three-Dimensional Printed Scaffolds for Osteochondral Regeneration. Tissue Engineering: Part A 21.1 (2015): 403-415.
Holmes, et al. Enhanced human bone marrow mesenchymal stem cell functions in novel 3D cartilage scaffolds with hydrogen treated multi-walled carbon nanotubes. Nanotechnology 24 (2013): 365102.
Holmes, et al. Testing of a 3D printed, nanostructured osteochondral implant for knee repair in a small animal model. May 15-17, 2017. 2017 TechConnect World Innovation Conference and Expo. National Harbor, Maryland.
Hung, et al. Synthesis and 3D Printing of Biodegradable Polyurethane Elastomer by a Water-Based Process for Cartilage Tissue Engineering Applications. Adv. Healthcare Mater. 3 (2014): 1578-1587.
Hung, et al. Water-based polyurethane 3D printed scaffolds with controlled release function for customized cartilage tissue engineering. Biomaterials 83 (2016): 156-168.
International search report with written opinion dated Dec. 6, 2017 for PCT/US2017/045792.
Kang, et al. A 3D bioprinting system to produce human-scale tissue constructs with structural integrity. Nature Biotechnology, 34.3 (2016): 312-319.
Kennedy, et al. Osteochondral Fractures of the Femoral Condyles. The Journal of Bone and Joint Surgery, 48.3 (1966): 436-440.
Klokkevold, et al. Advanced Implant Surgery and Bone Grafting Techniques. Clinical Periodontology, 9th ed. (2002): 905-921.
Kokubo, et al. Apatite-forming ability of alginate fibers treated with calcium hydroxide solution. Journal of Materials Science: Materials in Medicine 15 (2004): 1007-1012.
Kokubo, et al. How useful is SBF in predicting in vivo bone bioactivity?. Biomaterials 27 (2006): 2907-2915.
Kumar, et al. Mechanical strength of osteochondral junction. Nihon Seikeigeka Gakkai Zasshi. 65.11 (1991): 1070-7.
Kwakwa, et al. Engineering 3D Models of Tumors and Bone to Understand Tumor-Induced Bone Disease and Improve Treatments. Curr Osteoporos Rep 15 (2017): 247-254.

(56) References Cited

OTHER PUBLICATIONS

Lambertz, et al. Elastic mesh with thermoplastic polyurethane filaments preserves effective porosity of textile implants. Journal of Biomedical Materials Research, 103.8 (2015): 2654-2660.
Lee, et al. Recent advances in 3D printing of tissue engineering scaffolds. Methods Mol Bioi 868 (2012): 257-267.
McCracken, et al. Programming Mechanical and Physicochemical Properties of 3D Hydrogel Cellular Microcultures via Direct Ink Writing. Adv. Healthcare Mater. 5 (2016): 1025-1039.
Mi, et al. Morphology, mechanical properties, and mineralization of rigid thermoplastic polyurethane/hydroxyapatite scaffolds for bone tissue applications: effects of fabrication approaches and hydroxyapatite size. J Mater Sci 49 (2014): 2324-2337.
Mi, et al. Thermoplastic polyurethane/hydroxyapatite electrospun scaffolds for bone tissue engineering: effects of polymer properties and particle size. J Biomed Mater Res Part B, 102B.7 (2014): 1434-1444.
Michael, et al. Tissue Engineered Skin Substitutes Created by Laser-Assisted Bioprinting Form Skin-Like Structures in the Dorsal Skin Fold Chamber in Mice. PLOS ONE, 8.3 (2013): e57741.
Mitra, et al. Scaffolds for bone tissue engineering: role of surface patterning on osteoblast response. RSC Adv 3 (2013): 11073-11094.
Mok, et al. A review of materials currently used in orbital floor reconstruction. Can J Plast Surg 12.3 (2004): 134-140.
Naing, M. W. et al. Fabrication of customised scaffolds using computer-aided design and rapid prototyping techniques, Rapid Prototyping Journal, 2005, vol. 11, No. 4, pp. 249-259.
Notoya, et al. Enhancement of Osteogenesis In Vitro and In Vivo by a Novel Osteoblast Differentiation Promoting Compound, TAK-778. The Journal of Pharmacology and Experimental therapeutics, 290.3 (1999): 1054-1064.
Nowicki, et al. 3D printing of novel osteochondral scaffolds with graded microstructure. Nanotechnology 27 (2016): 414001.
O'Shea, et al. Bilayered Scaffolds for Osteochondral Tissue Engineering. Tissue Engineering: Part B, 14.4 (2008): 447-464.
Peter, et al. Polymer Concepts in Tissue Engineering. J Biomed Mater Res 43.4 (1998), 422-427.
Plecko, et al. Osseointegration and biocompatibility of different metal implants—a comparative experimental investigation in sheep. BMC Musculoskeletal Disorders, 13.32 (2012): 12 pages.
Rogers, et al. Autogenous bone graft: basic science and clinical implications. J Craniofac Surg 23.1 (2012): 323-327.
Saito, et al. Arrayed three-dimensional structures designed to induce and maintain a cell pattern by a topographical effect on cell behavior. Materials Science and Engineering C 49 (2015): 256-261.
Sandler, et al. Towards fabrication of 3D printed medical devices to prevent biofilm formation. International Journal of Pharmaceutics 459 (2014): 62-64.
Sansone, et al. The effects on bone cells of metal ions released from orthopaedic implants. A review. Clinical Cases in Mineral and Bone Metabolism, 10.1 (2013): 34-40.
Schaefer, et al. In vitro generation of osteochondral composites. Biomaterials 21 (2000): 2599-2606.
Schlicht, et al. Fibroblastic response and surface characterization of O2-plasma-treated thermoplastic polyetherurethane. Biomed. Mater. 5 (2010): 025002.
Seitz, et al. Three-Dimensional Printing of Porous Ceramic Scaffolds for Bone Tissue Engineering. J Biomed Mater Res B Appl Biomater. 74.2 (2005): 782-788.
Sharma, et al. Human Cartilage Repair with a Photoreactive Adhesive-Hydrogel Composite. Sci Transl Med. 5.167 (2013): 18 pages.
Sumanasinghe, et al. Mesenchymal stem cell-seeded collagen matrices for bone repair: Effects of cyclic tensile strain, cell density, and media conditions on matrix contraction in vitro. J Biomed Mater Res A. 88.3 (2008): 778-786.
Summers, et al. Donor Site Pain From The Ilium. J Bone Joint Surg, 71.4 (1989): 677-680.
Tack, et al. 3D-printing techniques in a medical setting: a systematic literature review. BioMed Eng OnLine, 15.115 (2016): 21 pages.
Tsai, et a. Biomimetic heterogenous elastic tissue development. npj Regenerative Medicine 2.16 (2017) : 8 pages.
Uddin, et al. Enhancement of Osteogenic Differentiation and Proliferation in Human Mesenchymal Stem Cells by a Modified Low Intensity Ultrasound Stimulation under Simulated Microgravity. Plos One, 8.9 (2013): e73914.
Wang, et al. Physical Shock Wave Mediates Membrane Hyperpolarization and Ras Activation for Osteogenesis in Human Bone Marrow Stromal Cells. Biochemical and Biophysical Research Communications 287 (2001): 648-655.
Webber, et al. A Perspective on the Clinical Translation of Scaffolds for Tissue Engineering. Ann Biomed Eng. 43.3 (2015): 641-656.
Wu, et al. A Biomimetic Hierarchical Scaffold: Natural Growth of Nanotitanates on Three-Dimensional Microporous Ti-Based Metals. Nano Lett., 8.11 (2008): 3803-3808.
Wu, et al. AICAR, a small chemical molecule, primes osteogenic differentiation of adult mesenchymal stem cells. Int J Artif Organs 34.12 (2011): 1128-1136.
Zhu, et al, A Novel Regulatory Role for Stromal-derived Factor-1 Signaling in Bone Morphogenic Protein-2 Osteogenic Differentiation of Mesenchymal C2C12 Cells. Journal of Biological Chemistry. 282.26 (2007): 18676-18685.
Zhu, et al. The effect of surface charge on hydroxyapatite nucleation. Biomaterials 25 (2004): 3915-3921.
Zindarsic, et al. Influence of surface charge and protein intermediary layer on the formation of biomimetic calcium phosphate on silica nanoparticles. J. Mater. Chem., 22 (2012): 19562-19569.

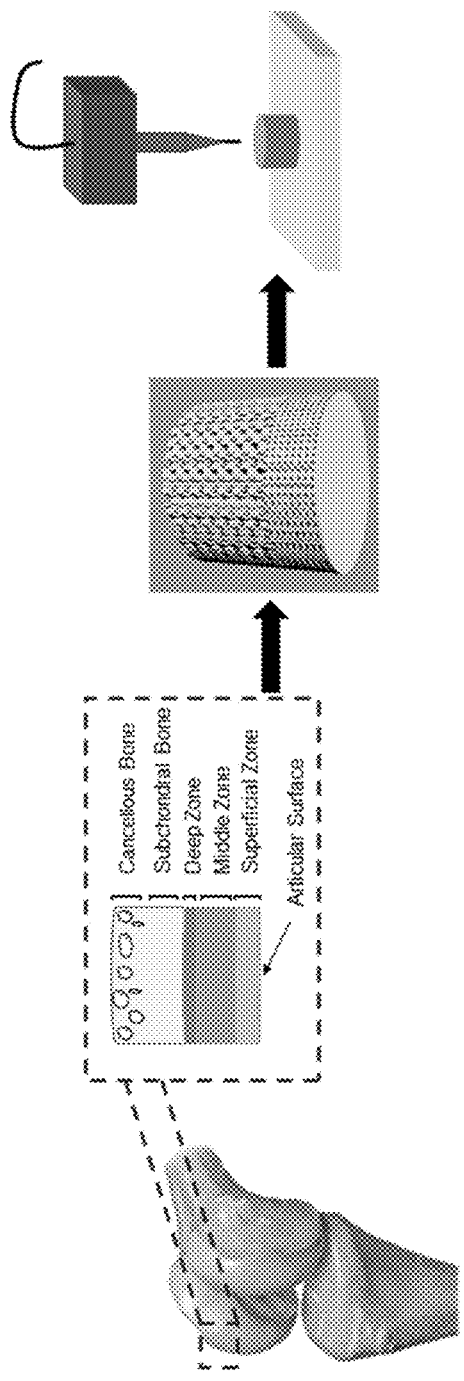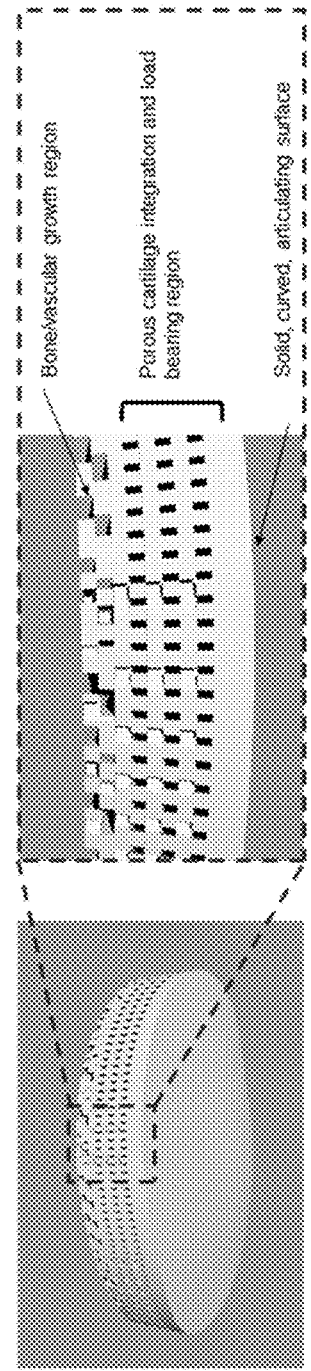
FIG. 16A
FIG. 16B

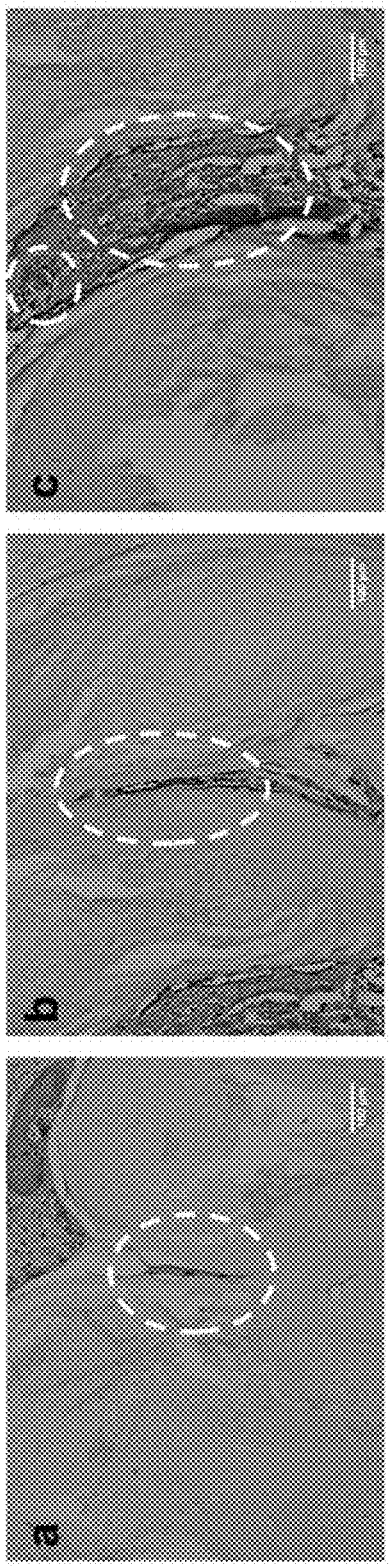

THREE-DIMENSIONALLY PRINTED TISSUE ENGINEERING SCAFFOLDS FOR TISSUE REGENERATION

CROSS-REFERENCE

This application claims the benefit of U.S. Provisional Application No. 62/371,805, filed Aug. 7, 2016, which application is incorporated herein by reference in its entirety.

BACKGROUND OF THE INVENTION

Large, critical-sized tissue defects (e.g., craniofacial, spinal, hip, and knee defects) comprising bone, vasculature, and cartilage damage caused by traumatic injury, cancer, or disease, may be challenging to treat owing to the size and complexity of the defects. Surgically implanting scaffolds and/or other forms of graft materials to promote tissue regeneration (e.g., bone and/or osteochondral regeneration) is a common approach in promoting tissue growth. Common sources of tissue grafts include autografts, allografts, and synthetic materials. Autologous and allologous sources are favored for their biocompatibility and minimized probability of disease transfection. However, several limitations exist including inadequate amounts of available autologous donor tissue and donor site morbidity. In addition, the amount of cadaveric donor tissue available from reserves is in limited supply.

In order to address such issues, metallic and synthetic materials, which closely match the mechanical properties of native tissue, have been adopted for large tissue defect repair. Current materials in use include metals such as titanium, cobalt, and stainless steel, as well as nonmetallic materials like hydroxyapatite, bioactive glass, or polymers. Metallic implants, though widely used as implantable fixtures due to their mechanical properties, often lead to pathological tissue deterioration as a result of corrosion. While some metallic implants have been modified for enhanced biocompatibility, they have also been found to release toxic ions deleteriously affecting local tissue. In an effort to address these concerns, nonmetallic synthetic materials, such as hydroxyapatite, have been employed due to their biocompatibility and manufacturability in the fabrication of porous three-dimensional (3D) structures. Although most inorganic ceramics exhibit effective bioactivity, the mechanical properties are inadequate for regeneration of native tissue. In addition, they can be difficult to process and manufacture.

Accordingly, there may exist a need for tissue engineering scaffolds made from a combination of biocompatible synthetic polymers and morphogenic factors in order to mimic the mechanical properties of native tissue and promote high levels of host-implant integration.

SUMMARY OF THE INVENTION

In one aspect, a three-dimensional tissue scaffold is provided comprising: (a) a first layer comprising a first material and having a plurality of first pores, each comprising a first average pore width; (b) a second layer comprising a second material and having a plurality of second pores, each having a second average pore width; wherein a surface of the first layer, the second layer, or both comprise a plurality of pits having an average width that is below the resolution of a rapid prototyping technology. In some cases, the plurality of pits have an average width of about 200 nm to about 50 μm. In some cases, the first average pore width and the second average pore width are different. In some cases, the first material and the second material are different. In some cases, the first material and the second material are the same. In some cases, the first material, the second material, or both comprises a composite material comprising an insoluble component and soluble component that has been immersed in a solvent. In some cases, the soluble component of the composite material has been dissolved by the solvent. In some cases, the solvent is water. In some cases, the at least one insoluble component is selected from the group consisting of: thermoplastic polyurethane (TPU), polycaprolactone (PCL), poly co-glycolic acid (PLGA), polylactic acid (PLA), and high impact polystyrene (HIPS). In some cases, the at least one soluble component is selected from the group consisting of: Polyvinyl alcohol (PVA), salt, sugar or sugar glass, polyethylene glycol (PEG) or any uncrosslinked functionalized derivative thereof, gelatin or any derivative thereof, poly co-glycolic acid (PLGA), alginate, and sodium bicarbonate. In some cases, the insoluble component is TPU and the soluble component is PVA. In some cases, the composite material comprises about 70 wt % TPU and about 30 wt % PVA. In some cases, the composite material comprises from about 50 wt % insoluble component to about 95 wt % insoluble component. In some cases, the composite material comprises from about 5 wt % soluble component to about 50 wt % soluble component. In some cases, the first average pore width is from about 0 μm to about 50 μm. In some cases, the second average pore width is from about 100 μm to about 200 μm. In some cases, at least one of the first layer and the second layer is fabricated using at least one rapid prototyping technology. In some cases, the at least one rapid prototyping technology is stereolithography (SLA). In some cases, the at least one rapid prototyping technology is digital light processing (DLP). In some cases, the at least one rapid prototyping technology is fused deposition modeling (FDM). In some cases, the at least one rapid prototyping technology is selective laser sintering (SLS). In some cases, the at least one rapid prototyping technology is selective laser melting (SLM). In some cases, the at least one rapid prototyping technology is electron beam melting (EBM). In some cases, the at least one rapid prototyping technology is laminated object manufacturing (LOM). In some cases, the at least one rapid prototyping technology is bio-plotting. In some cases, the at least one rapid prototyping technology is deposition printing. In some cases, the first layer and the second layer are fabricated using a different rapid prototyping technology. In some cases, the first layer and the second layer are fabricated using the same rapid prototyping technology. In some cases, the three-dimensional tissue scaffold has a size and shape corresponding to a size and shape of a tissue defect. In some cases, the tissue defect is a large critical-sized tissue defect. In some cases, each of the first pore width and the second pore width corresponds to a different tissue type. In some cases, the tissue type is bone, cartilage, connective tissue, or skeletal tissue. In some cases, each of the first layer and the second layer is capable of supporting a plurality of different cell types. In some cases, the three-dimensional tissue scaffold further comprises a third material and has a plurality of third pores, each having a third average pore width. In some cases, the third average pore width is larger than the second average pore width. In some cases, the first average pore width, the second average pore width, and the third average pore width are substantially the same. In some cases, the third average pore width is from about 500 μm to about 1 mm. In some cases, any one of the plurality of first pores and the plurality of second pores is arranged in a predetermined geometric pattern. In some cases, the predetermined geometric pattern is a voronoi structure. In some cases, the three-dimensional tissue scaffold is fabricated based on medical imaging data. In some cases, the plurality of first pores, the plurality of second pores, or both have a shape selected from the group consisting of: hexagonal, polygonal, circular, square, rectangular, and triangular. In some cases, the three-dimensional tissue scaffold has a cylindrical shape. In some cases, the three-dimensional tissue scaffold has an elliptical cross-section. In some cases, the three-dimensional tissue scaffold has an irregular shape. In some cases, the three-dimensional tissue scaffold has a shape that is customizable.

In another aspect, a three-dimensional tissue scaffold is provided comprising: (a) a first layer comprising a first material and having a plurality of first pores, each comprising a first average pore width; (b) a second layer comprising a second material and having a plurality of second pores, each having a second average pore width; and wherein at least one of the first material and the second material comprises a composite material having an insoluble component and a soluble component. In some case, the second average pore width is greater than the first average pore width. In some cases, the first average pore width and the second average pore width are substantially the same. In some cases, when the tissue scaffold is immersed in a solvent, the soluble component is dissolved, thereby leaving behind the insoluble component. In some cases, the solvent is water. In some cases, when the tissue scaffold is immersed in a solvent, a plurality of pits are formed along a surface of a fiber of the insoluble component. In some cases, the plurality of pits have an average pore width ranging from about 200 nm to about 50 μm. In some cases, the three-dimensional tissue scaffold further comprises: (c) a third layer comprising a third material and having a plurality of third pores, each having a third average pore width. In some cases, the third average pore width is larger than the second average pore width. In some cases, the first average pore width, the second average pore width, and the third average pore width are substantially the same. In some cases, the third average pore width is from about 500 μm to about 1 mm. In some cases, the first average pore width is from about 0 μm to about 50 μm. In some cases, the second average pore width is from about 100 μm to about 200 μm. In some cases, the at least one insoluble component is selected from the group consisting of: thermoplastic polyurethane (TPU), polycaprolactone (PCL), poly co-glycolic acid (PLGA), polylactic acid (PLA), and high impact polystyrene (HIPS). In some cases, the at least one soluble component is selected from the group consisting of: Polyvinyl alcohol (PVA), salt, sugar or sugar glass, polyethylene glycol (PEG) or any uncrosslinked functionalized derivative thereof, gelatin or any derivative thereof, poly co-glycolic acid (PLGA), alginate, and sodium bicarbonate. In some cases, the insoluble component is TPU and the soluble component is PVA. In some cases, the composite material comprises about 70 wt % TPU and about 30 wt % PVA. In some cases, the composite material comprises a range from about 50 wt % insoluble component to about 95 wt % insoluble component. In some cases, the composite material comprises a range from about 5 wt % soluble component to about 50 wt % soluble component. In some cases, the first material and the second material are the same. In some cases, the first material and the second material are different. In some cases, any one of the plurality of first pores and the plurality of second pores is arranged in a predetermined geometric pattern. In some cases, the predetermined geometric pattern is a voronoi structure. In some cases, the three-dimensional tissue scaffold is fabricated based on medical imaging data. In some cases, the plurality of first pores, the plurality of second pores, or both have a shape selected from the group consisting of: hexagonal, polygonal, circular, square, rectangular, and triangular. In some cases, the three-dimensional tissue scaffold has a cylindrical shape. In some cases, the three-dimensional tissue scaffold has an elliptical cross-section. In some cases, the three-dimensional tissue scaffold has an irregular shape. In some cases, the three-dimensional tissue scaffold has a shape that is customizable. In some cases, at least one of the first layer and the second layer is fabricated using a rapid prototyping technology. In some cases, the rapid prototyping technology is selected from the group consisting of: stereolithography (SLA), digital light processing (DLP), fused deposition modeling (FDM), selective laser sintering (SLS), selective laser melting (SLM), electron beam melting (EBM), laminated object manufacturing (LOM), bio-plotting, and deposition printing. In some cases, the first layer and the second layer are fabricated using a different rapid prototyping technology. In some cases, the first layer and the second layer are fabricated using a same rapid prototyping technology. In some cases, the three-dimensional tissue scaffold has a size and shape corresponding to a size and shape of a tissue defect. In some cases, the tissue defect is a large critical-sized tissue defect. In some cases, each of the first pore width and the second pore width corresponds to a different tissue type. In some cases, the tissue type is bone, cartilage, connective tissue, or skeletal tissue. In some cases, each of the first layer and the second layer is capable of supporting a plurality of different cell types.

In another aspect, a method for manufacturing a three-dimensional tissue scaffold is provided, the method comprising: (a) fabricating a first layer comprising a plurality of first pores; (b) fabricating a second layer comprising a plurality of second pores, wherein at least one of the first layer and the second layer comprises a composite material having an insoluble component and a soluble component; and (c) dissolving the soluble component from the composite material, thereby manufacturing the three-dimensional tissue scaffold. In some cases, the three-dimensional tissue scaffold, after the dissolving of (c), comprises a plurality of pits along a surface of the insoluble component. In some cases, the plurality of pits comprises an average width below the resolution of a rapid prototyping technology. In some cases, the plurality of pits comprises an average width of about 200 nm to about 50 μm. In some cases, the fabricating of (a), (b), or both comprises performing one or more rapid prototyping technologies. In some cases, the one or more rapid prototyping technologies comprises stereolithography (SLA). In some cases, the one or more rapid prototyping technologies comprises digital light processing (DLP). In some cases, the one or more rapid prototyping technologies comprises fused deposition modeling (FDM). In some cases, the one or more rapid prototyping technologies comprises selective laser sintering (SLS). In some cases, the one or more rapid prototyping technologies comprises selective laser melting (SLM). In some cases, the one or more rapid prototyping technologies comprises electron beam melting (EBM). In some cases, the one or more rapid prototyping technologies comprises laminated object manufacturing (LOM). In some cases, the one or more rapid prototyping technologies comprises bio-plotting. In some cases, the one or more rapid prototyping technologies comprises deposition printing. In some cases, the method further comprises, prior to (a), determining a three-dimensional shape of a tissue defect of a patient. In some cases, the determining comprises performing a computed tomography (CT) scan, a magnetic resonance imaging (MRI) scan, or both. In some cases, the three-dimensional tissue scaffold corresponds to the three-dimensional shape of the tissue defect. In some cases, the tissue defect is a large critical-sized tissue defect. In some cases, the dissolving of (c) comprises immersing the first layer and the second layer in a solvent. In some cases, the dissolving of (c) comprises sonicating the three-dimensional tissue scaffold in the solvent. In some cases, the insoluble component is selected from the group consisting of: thermoplastic polyurethane (TPU), polycaprolactone (PCL), poly co-glycolic acid (PLGA), polylactic acid (PLA), and high impact polystyrene (HIPS). In some cases, the soluble component is selected from the group consisting of: Polyvinyl alcohol (PVA), salt, sugar or sugar glass, polyethylene glycol (PEG) or any uncrosslinked functionalized derivative thereof, gelatin or any derivative thereof, poly co-glycolic acid (PLGA), alginate, and sodium bicarbonate. In some cases, the insoluble component is TPU and the soluble component is PVA. In some cases, the composite material comprises about 70 wt % TPU and about 30 wt % PVA. In some cases, the composite material comprises from about 50 wt % insoluble component to about 95 wt % insoluble component. In some cases, the composite material comprises from about 5 wt % soluble component to about 50 wt % soluble component. In some cases, the first average pore width is from about 0 µm to about 50 µm. In some cases, the second average pore width is from about 100 µm to about 200 µm.

In yet another aspect, a three-dimensional tissue scaffold is provided comprising a plurality of pores and a plurality of pits, wherein a pore width of the plurality of pores changes in size along a gradient from a first region to a second region, and the plurality of pits has an average width below the resolution of a rapid prototyping technology. In some cases, the plurality of pits has an average width of about 200 nm to about 50 µm. In some cases, the gradient is described by a linear function. In some cases, the gradient is described by a step function having at least 3 steps. In some cases, the gradient is described by a sigmoidal function. In some cases, the first region of the scaffold comprises a first material and the second region of the scaffold comprises a second material.

In yet another aspect, a three-dimensional tissue scaffold is provided comprising a first material, and comprising a plurality of pits having an average width below the resolution of a rapid prototyping technology. In some cases, the three-dimensional tissue scaffold comprises at least one composite material having an insoluble component and a soluble component. In some cases, the first material comprises a composite material comprising an insoluble component and soluble component that has been immersed in a solvent. In some cases, the soluble component of the composite material has been dissolved by the solvent. In some cases, the solvent is water. In some cases, the insoluble component is selected from the group consisting of: thermoplastic polyurethane (TPU), polycaprolactone (PCL), poly co-glycolic acid (PLGA), polylactic acid (PLA), and high impact polystyrene (HIPS). In some cases, the soluble component is selected from the group consisting of: Polyvinyl alcohol (PVA), salt, sugar or sugar glass, polyethylene glycol (PEG) or any uncrosslinked functionalized derivative thereof, gelatin or any derivative thereof, poly co-glycolic acid (PLGA), alginate, and sodium bicarbonate. In some cases, the composite material comprises from about 50 wt % insoluble component to about 95 wt % insoluble component. In some cases, the composite material comprises from about 5 wt % soluble component to about 50 wt % soluble component. In some cases, the insoluble component is TPU and the soluble component is PVA. In some cases, the composite material comprises about 70 wt % TPU and about 30 wt % PVA.

In yet another aspect, a three-dimensional tissue scaffold is provided comprising: a first layer having a plurality of first pores, wherein an average pore width of the plurality of first pores is from 0 to about 50 µm; a second layer attached to a side of the first layer and having a plurality of second pores, wherein an average pore width of the plurality of second pores is from about 100 µm to about 200 µm; and a third layer attached to a side of the second layer and having a plurality of third pores, wherein an average pore width of the plurality of third pores is from about 500 µm to about 1 mm, wherein at least one of the first layer, the second layer, or the third layer comprises a plurality of pits having an average width below the resolution of a rapid prototyping technology. In some cases, the first layer has an average thickness of less than about 0.5 mm. In some cases, the second layer has an average thickness of about 1.5 mm to about 3 mm. In some cases, the third layer has an average thickness of less than about 0.5 mm. In some cases, the three-dimensional tissue scaffold has a cylindrical shape.

In yet another aspect, a method is provided for treating a subject having a tissue defect, the method comprising: surgically implanting a three-dimensional tissue scaffold according to any one of the above aspects into the tissue defect of the subject, thereby treating the subject. In some cases, the tissue defect is a large, critical-sized tissue defect. In some cases, the method further comprises, prior to surgically implanting, nucleating the three-dimensional tissue scaffold. In some cases, the nucleating comprises incubating the three-dimensional tissue scaffold in a simulated bodily fluid (SBF). In some cases, the method further comprises, prior to surgically implanting, coating the three-dimensional tissue scaffold with nano-hydroxyapatite (nHA) or tricalcium phosphate (TCP). In some cases, the coating comprises spray coating or absorption coating. In some cases, the subject is a human. In some cases, the subject is an equine.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 16A depicts a schematic illustration of a non-limiting example of an osteochondral implant fabrication process according to various embodiments of the disclosure.

FIG. 16B depicts a computer-aided design (CAD) model of a non-limiting example of an osteochondral implant according to various embodiments of the disclosure.

FIGS. 20A-20C depict H&E staining of TPU samples at 3 months of healing according to various embodiments of the disclosure.

DETAILED DESCRIPTION OF THE INVENTION

Figure 1A:
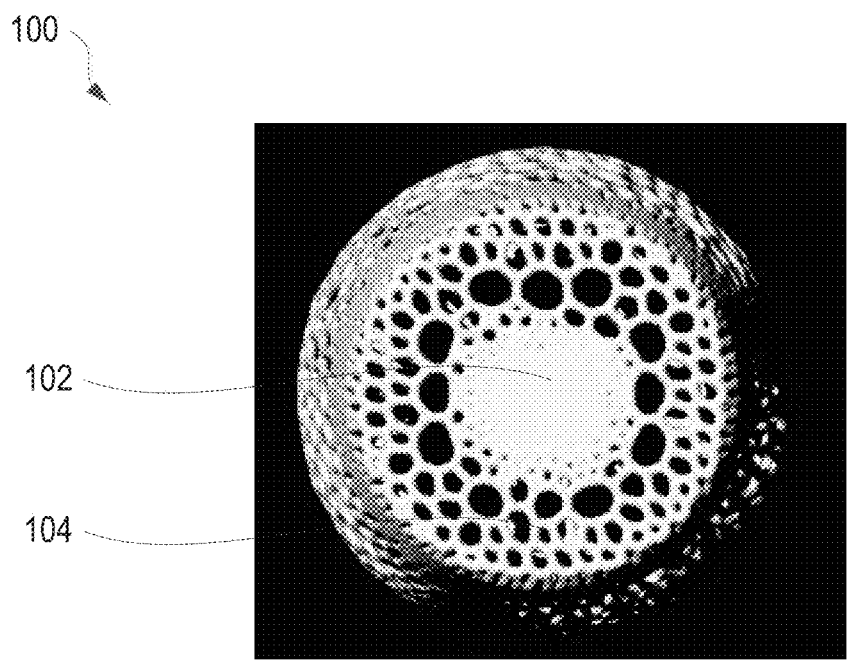
FIG. 1A depicts a top view of an exemplary tissue engineering scaffold according to one or more aspects of the present disclosure.

In the following description of the various examples and components of this disclosure, reference is made to the accompanying drawings, which form a part hereof, and in which are shown by way of illustration various example structures and environments in which aspects of the disclosure may be practiced. It is to be understood that other structures and environments may be utilized and that structural and functional modifications may be made from the specifically described structures and methods without departing from the scope of the present disclosure.

Also, while the terms "top," "bottom," "front," "back," "side," "rear," "upward," "downward," and the like may be used in this specification to describe various example features and elements of the invention, these terms are used herein as a matter of convenience, e.g., based on the example orientations shown in the figures or the orientation used during typical use. Additionally, the term "plurality," as used herein, indicates any number greater than one, either disjunctively or conjunctively, as necessary, up to an infinite number. Nothing in the specification should be construed as requiring a specific three-dimensional orientation of structures in order to fall within the scope of this invention. Also, the reader is advised that the drawings are not necessarily drawn to scale.

Disclosed herein are three-dimensional tissue scaffolds for, e.g., the repair of tissue defects, as well as methods for manufacturing tissue scaffolds and methods of using tissue scaffolds for the repair of tissue defects. In particular aspects, the three-dimensional tissue scaffolds may be used to treat large tissue defects, such as large, critical-sized tissue defects. Generally, the tissue scaffolds of the disclosure are biocompatible, porous structures that are capable of supporting the growth and repair of multiple different tissue and cell types. The three-dimensional tissue scaffolds disclosed herein may include one or more layers fabricated from one or more materials. In some aspects, at least one of the layers is fabricated from a composite material that includes an insoluble component and a soluble component. The soluble component may be dissolved from the scaffold structure creating a tissue scaffold having a unique micro- and/or nanoporous structure that is, e.g., capable of supporting adhesion and growth of multiple different cell types. The three-dimensional tissue scaffolds of the disclosure may be manufactured to correspond to the three-dimensional size and/or shape of the tissue defect and may be manufactured by any number of rapid prototyping techniques.

Three-Dimensional Tissue Scaffolds

In some aspects, a three-dimensional tissue scaffold is provided comprising: (a) a first layer comprising a first material and having a plurality of first pores, each comprising a first average pore width; (b) a second layer comprising a second material and having a plurality of second pores, each having a second average pore width. In some cases, at least one of the first material and the second material comprises a composite material having an insoluble component and a soluble component. Generally, the three-dimensional tissue scaffolds disclosed herein comprise a composite material that includes an insoluble component and a soluble component. The tissue scaffold may be exposed to or contacted with a solvent that is capable of dissolving the soluble component, leaving the insoluble component intact and in substantially the same shape and/or size as fabricated. The term "insoluble component" as used herein may refer to a material that does not dissolve or does not substantially dissolve in a given solvent. The term "soluble component" as used herein may refer to a material that is capable of dissolving in a given solvent. Non-limiting examples of solvents may include, without limitation, acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether), 1,2-dimethoxy-ethane (glyme, DME), dimethyl-formamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroin), 1-propanol, 2-propanol, pyridine, tetrahydrofuran (THF), toluene, triethyl amine, o-xylene, m-xylene, p-xylene, and D-limonene.

In some cases, the three-dimensional tissue scaffold comprises a composite material having a component that is insoluble in water, and another component that is soluble in water. In this example, immersing the tissue scaffold in water may dissolve the soluble component, leaving the insoluble component intact. Non-limiting examples of water-insoluble components that may be used in the three-dimensional tissue scaffolds of the disclosure may include: thermoplastic polyurethane (TPU), polycaprolactone (PCL), poly co-glycolic acid (PLGA), polylactic acid (PLA), and high impact polystyrene (HIPS). Non-limiting examples of water-soluble components that may be used in the three-dimensional tissue scaffolds of the disclosure may include: polyvinyl alcohol (PVA), salt, sugar or sugar glass, polyethylene glycol (PEG) and any un-crosslinked functionalized derivative thereof (such as PEGDA), gelatin and any derivative thereof (such as gelatin methacrylate), poly co-glycolic acid (PLGA), alginate, and sodium bicarbonate and other effervescent materials. In a particular example, the insoluble component is thermoplastic polyurethane (TPU) and the soluble component is polyvinyl alcohol (PVA).

The composite material may comprise an insoluble component in an amount ranging from about 50 wt % of the composite material to about 95 wt % of the composite material. For example, the insoluble component may be present in the composite material in the amount that is about: 50-95 wt %, 55-90 wt %, 60-85 wt %, 65-80 wt %, 60-80 wt %, 65-75 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, or 95 wt % of the composite material.

In some examples, the composite material may comprise the insoluble component in an amount that is at least 50 wt % of the composite material. For example, the insoluble component may be present in the composite material in the amount that is at least: 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, or 95 wt % of the composite material.

The composite material may comprise a soluble component in an amount ranging from about 5 wt % of the composite material to about 50 wt % of the composite material. For example, the soluble component may be present in the composite material in the amount that is about: 5-50 wt %, 10-45 wt %, 15-40 wt %, 20-40 wt %, 25-35 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, or 50 wt % of the composite material.

In some examples, the composite material may comprise the soluble component in an amount that is no more than 50 wt % of the composite material. For example, the soluble component may be present in the composite material in the amount that is no more than: 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, or 50 wt % of the composite material.

In a non-limiting example, the composite material comprises about 70% wt insoluble component (e.g., TPU) and about 30% wt soluble component (e.g., PVA).

In some cases, the three-dimensional tissue scaffold is a heterogeneous construct fabricated from a plurality of materials. For example, the tissue scaffold may have more than one layer (e.g., biphasic, triphasic), each layer fabricated from a different material. In some examples, the tissue scaffold may have more than one layer, with at least one layer fabricated from a composite material including an insoluble component and a soluble component. In some cases, the additional layers may be fabricated from a material other than the composite material. Examples of additional materials that may be used to fabricate a tissue scaffold are known in the art and may include, without limitation, polylactic acid (PLA), poly-L-lactic acid (PLLA), polyglycolic acid (PLGA), polycaprolactone (PCL), polydioxanone (PDO), collagen, fibrin and derivatives thereof, polysaccharides (e.g., chitosan), glycosaminoglycans (e.g., hyaluronic acid), fibrinogen, or gelatin. In some cases, the additional layers may be fabricated from a different composite material, such as a composite material having different insoluble and/or soluble components.

In some aspects, the three-dimensional tissue scaffold is a homogeneous construct fabricated from a single material. For example, the tissue scaffold may be fabricated from a single material or from a composite material having the same insoluble and soluble components. In one example, the tissue scaffold may have more than one layer (e.g., biphasic, triphasic, etc.), each layer fabricated from the same composite material (i.e., having the same soluble and insoluble components). In another example, the tissue scaffold may have more than one layer (e.g., biphasic, triphasic, etc.), each layer fabricated with a different composition of the same composite material. For example, each layer may be fabricated with a composite material having the same soluble and insoluble components, however, each layer may have a different amount of soluble and insoluble components. By way of example only, one layer may be fabricated from a composite material having 70 wt % of insoluble component and 30 wt % of soluble component, and another layer may be fabricated from a composite material having 50 wt % of the same insoluble component and 50 wt % of the same soluble component. Without wishing to be bound by theory, varying the ratios of insoluble component to soluble component may alter the micro- and/or nano-structure (e.g., size of surface pits) of the scaffold. In this way, tissue scaffolds may be designed with different regions or layers that correspond to different tissue and/or cell types. For example, neuronal cells have been documented to respond to nano-scale pores and channels of 10 to 30 nm, while osteoblasts respond to pores of 50 to 100 nm. These pores sizes and distributions may be modulated by adjusting the composition percentage of soluble (temporary) to insoluble (permanent) material.

In some aspects, a three-dimensional tissue scaffold of the disclosure may be porous, for example, the tissue scaffold may comprise a plurality of pores. The plurality of pores may have any number or variety of shapes. For example, the pores may have a hexagonal, polygonal, circular, square, rectangular, and triangular shape. Each of the plurality of pores may have a pore width (and collectively may have an average pore width). In some cases, the plurality of pores may be fabricated in any one, or combination of, a voronoi structure and/or a pre-designed geometric pattern including a plurality of sides and angles, as described further throughout. Pore widths and/or heights may range in size from about 1 µm to about 5 mm, for example from about 1 µm to about 50 µm, from about 10 µm to about 100 µm, from about 50 µm to about 250 µm, from about 150 µm to about 500 µm, from about 650 µm to about 1 mm, or from about 1 mm to about 5 mm. For example, pores may be about 1 µm, 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, or 5 mm in width and/or height. Pore sizes may vary throughout the tissue scaffold, and may be determined by e.g., the rapid prototyping technique employed during fabrication of each layer, or the pattern in which the layers are printed. Dissolution of the soluble component from each layer may further superimpose a micro- or nanoporosity on a surface (e.g., plurality of pits on a fiber of the insoluble component) as further described herein.

In some aspects, a three-dimensional tissue scaffold of the disclosure may comprise a first layer having a plurality of first pores with a first average pore width. The three-dimensional tissue scaffold may further comprise a second layer having a plurality of second pores with a second average pore width. In some cases, the first average pore width and the second average pore width are different. In some cases, a three-dimensional tissue scaffold of the disclosure may further comprise a third layer having a plurality of third pores, each comprising a third average pore width. In some cases, the third average pore width may be different from the first average pore width, the second average pore width, or both. In some cases, the first average pore width, the second average pore width, and the third average pore width are the same or substantially the same.

Further provided herein are three-dimensional tissue scaffolds comprising two or more layers having an increasingly larger average pore width. For example, a three-dimensional tissue scaffold may have a first layer having a plurality of pores of a first average pore width and a second layer having a plurality of pores of a second average pore width, wherein the second average pore width is greater than the first average pore width. In some instances, a three-dimensional tissue scaffold may further have a third layer having a plurality of pores of a third average pore width, wherein the third average pore width is greater than the first and the second average pore widths. In some cases, each layer of the tissue scaffold may be fabricated to match a porosity associated with a particular tissue type (e.g., bone, cartilage, etc.). In some aspects, at least one layer is fabricated with a composite material having an insoluble and soluble component.

In another aspect, a three-dimensional tissue scaffold is provided comprising a plurality of pores, wherein a pore width of the plurality of pores changes in size along a gradient from a first region to a second region. In other words, a device may have discrete regions that change pore size in succession, or the size of the pores may change very gradually from a starting size to an ending size, based on a linear or non-linear change. This formation of a gradient is may be an important mechanism for stem cell development and new tissue growth, especially for skeletal tissue and complex tissue. In some cases, the first region and second region are regions within a first layer and a second layer, respectively. In some cases, the first layer and second layer are fabricated from different materials. In other cases, the first region and second region are regions within the same layer. In some cases, the gradient may be described by a linear function. In other cases, the gradient may be described by a step function. The step function may have at least 3 steps, for example, at least 3 steps, at least 4 steps, at least 5 steps, at least 6 steps, at least 7 steps, at least 8 steps, at least 9 steps, or at least 10 steps. In other cases, the gradient may be described by a sigmoidal function.

In scenarios where the tissue scaffold has more than one layer, each layer may have a different average pore width. In some cases, each layer may have the same or a similar average pore width. In some cases, each layer of the tissue scaffold may comprise the same material. In other cases, each layer of the tissue scaffold may comprise a different material. Generally, at least one layer of the tissue scaffold is fabricated with a composite material having an insoluble component and a soluble component. In some cases, each layer of the tissue scaffold is fabricated using the same rapid prototyping technique. In other cases, each layer of the tissue scaffold is fabricated using a different rapid prototyping technique. The tissue scaffold may have any number of layers. For example, the tissue scaffold may have 1, 2, 3, 4, 5, 6, 7, 8, 9, 10 or more than 10 layers.

In some cases, a tissue scaffold of the disclosure may have one or more layers, each layer having a thickness. In some cases, a thickness of the layer may be from about 0.1 mm to about 5 mm. For example, a layer may have a thickness of about 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, or 5.0 mm.

The three-dimensional tissue scaffold may be fabricated in essentially any desired shape and size. In some cases, the tissue scaffold will be designed to match the shape and size of a tissue defect. In other cases, the tissue scaffold may be designed to match the shape and size of a surgical incision. In one example, the three-dimensional tissue scaffold is a hollow cylinder or has a cylindrical shape. In another example, the tissue scaffold is a non-circular cylinder (e.g., has an elliptical cross-section). In yet another example, the tissue scaffold is an irregular shape (e.g., designed to match an irregular shape of a tissue defect). In another example, the tissue scaffold has a shape customized to match the shape of a tissue defect. The tissue scaffold may further comprise a size that matches the size of a tissue defect. The tissue scaffold may, for example, have a size ranging from about 1 to about 4 mm in thickness, and about 6 mm to about 2 cm in diameter Generally, the porosity and/or density of the tissue scaffold will be designed to correspond with the porosity and/or density of the tissue in which the tissue scaffold will be implanted. For example, if the tissue scaffold is to be implanted into a tissue defect involving bone, the tissue scaffold may have a porosity and/or density that is similar to or the same as bone. Often, the tissue defect will involve a complex arrangement of multiple different tissue and cell types, such that the tissue scaffold may be designed to have multiple regions or layers that correspond to the multiple different tissue and cell types. In some cases, a single layer of the tissue scaffold fabricated from a single material (e.g., a composite material), may be capable of supporting the growth and regeneration of multiple different cell types.

In a non-limiting example, a three-dimensional tissue scaffold may have a first layer having a plurality of first pores, wherein an average pore width of the plurality of first pores is from 0 to about 50 µm. For example, the average pore size of the first layer may be about 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, or 50 µm. In another example, a tissue scaffold may further have a second layer attached to a side of the first layer and having a plurality of second pores, wherein an average pore width of the plurality of second pores is from about 100 µm to about 200 µm. For example, the average pore size of a second layer may be about 100 µm, 110 µm, 120 µm, 130 µm, 140 µm, 150 µm, 160 µm, 170 µm, 180 µm, 190 µm, or about 200 µm. In another example, a tissue scaffold may further have a third layer attached to a side of the second layer and having a plurality of third pores, wherein an average pore width of the plurality of third pores is from about 500 µm to about 1 mm. For example, the average pore size of a third layer may be about 500 µm, 550 µm, 600 µm, 650 µm, 700 µm, 750 µm, 800 µm, 850 µm, 900 µm, 950 µm, or 1 mm. In some cases, at least one of the first layer, the second layer, or the third layer is fabricated with a composite material having an insoluble component and a soluble component.

In various aspects of the disclosure, the three-dimensional tissue scaffold may be exposed to or immersed in a solvent that is capable of dissolving the soluble component from the scaffold such that the insoluble component remains in the scaffold. In preferred cases, the insoluble component remains essentially intact (e.g., the same shape and/or size) as fabricated in the scaffold, after dissolution of the soluble component. The soluble component generally will be dissolved from the tissue scaffold prior to use. Dissolution of the soluble component can be performed by the manufacturer and sold to an end-user (e.g., a physician), or may be performed by an end-user. In some cases, the tissue scaffold is sold (e.g., in a kit) or otherwise provided to an end-user after dissolution of the soluble component.

In particular aspects of the disclosure, dissolution of the soluble component may generate a plurality of pits along a surface of the insoluble material. In a non-limiting example in which a tissue scaffold is fabricated using TPU/PVA, the tissue scaffold may be immersed in or otherwise contacted with water to dissolve the PVA component, such that the TPU component remains essentially intact in the shape and/or size as it was originally fabricated, however, the remaining insoluble component may comprise a plurality of pits along a surface (e.g., of a fiber). Without wishing to be bound by theory, the plurality of pits may create a unique stratified micro- and/or nano-structure that is capable of supporting the growth of a plurality of different cell types and the regeneration of a plurality of different tissue types. In some cases, the plurality of pits generated by dissolution of the soluble component may have a size (e.g., an average width) that is below the resolution of a rapid prototyping technology (e.g., below 50 µm). The plurality of pits generated by dissolution of the soluble component may have a size ranging from about 1 nm to about 50 µm, for example, from about 1 nm to about 10 nm, from about 5 nm to about 50 nm, from about 50 nm to about 150 nm, from about 125 nm to about 200 nm, from about 150 nm to about 500 nm, from about 250 nm to about 1 µm, from about 750 nm to about 5 µm, from about 5 µm to about 25 µm, or from about 10 µm to about 50 µm. For example, the plurality of pits may have a size of about 1 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 µm, 5 µm, 10 µm, 15 µm, 20 µm, 25 µm, 30 µm, 35 µm, 40 µm, 45 µm, or 50 µm. In some cases, the size of the pits is below the resolution of standard three-dimensional printers.

In some aspects, the three-dimensional tissue scaffolds of the disclosure may have an elastic modulus, after dissolution of the soluble component, ranging from about 1 MPa to about 1000 MPa, from example, from about 1 MPa to about 50 MPa, from about 50 MPa to about 500 MPa, from about 50 MPa to about 100 MPa, from about 100 MPa to about 500 MPa, from about 250 MPa to about 750 MPa, or from about 500 MPa to about 1000 MPa. For example, the elastic modulus of a tissue scaffold, after dissolution of the soluble component, may be about 1 MPa, 5 MPa, 10 MPa, 25 MPa, 50 MPa, 75 MPa, 100 MPa, 125 MPa, 150 MPa, 175 MPa, 200 MPa, 225 MPa, 250 MPa, 275 MPa, 300 MPa, 325 MPa, 350 MPa, 375 MPa, 400 MPa, 425 MPa, 450 MPa, 475 MPa, 500 MPa, 525 MPa, 550 MPa, 575 MPa, 600 MPa, 625 MPa, 650 MPa, 675 MPa, 700 MPa, 725 MPa, 750 MPa, 775 MPa, 800 MPa, 825 MPa, 850 MPa, 875 MPa, 900 MPa, 925 MPa, 950 MPa, 975 MPa, or 1000 MPa. In some cases, the elastic modulus of the tissue scaffold, after dissolution of the soluble component, is similar to that of calcified cartilage.

In some aspects, the tissue scaffold may be coated prior to implantation of the scaffold into a subject. Non-limiting examples of coatings that may be employed include nano-hydroxyapatite (nHa) coatings, tricalcium phosphate (TCP) coatings, and antibacterial metal-based nanoparticles. In some cases, the tissue scaffold is nucleated prior to implantation, by, e.g., incubating in a simulated bodily fluid (SBF), to promote bone regeneration. The three-dimensional tissue scaffolds may further be coated with any number of bioactive factors that may promote growth and/or regeneration of tissue. Non-limiting examples may include: growth factors, hormones, morphogenetic factors, such as bone morphogenic protein (BMP) and derivatives thereof, vascular endothelial growth factor (VEGF) and derivatives thereof, transformative growth factor (TGF) and derivatives thereof, as well as any amine linkage or amino acid group isolated from or intended to replicate specific portions of these growth factors.

Methods

Provided herein are methods for manufacturing a three-dimensional tissue scaffold of the disclosure. In one aspect, a method for manufacturing a three-dimensional tissue scaffold comprises fabricating a first layer comprising a plurality of first pores. The method may further comprise fabricating a second layer comprising a plurality of second pores. The scaffold may be manufactured from a plurality of materials through a plurality of manufacturing processes. For example, a top, center, and/or inner portion of scaffold may be manufactured from a first material (e.g., a composite material having an insoluble and soluble component) through a first manufacturing process (e.g., selective laser sintering) and a bottom, outer, and/or external portion of the scaffold may be manufactured from a second material (e.g., a non-composite material) through a second manufacturing process (e.g., fused deposition modeling). In some instances, the scaffold may be manufactured from a plurality of materials through a single manufacturing process. Generally, the scaffold will be manufactured such that at least one layer is fabricated from a composite material having an insoluble component and a soluble component. Non-limiting examples of tissue scaffolds fabricated from a composite material having an insoluble component and a soluble component have been described throughout. The method may further comprise dissolving the soluble component from the composite material. The dissolution step may be performed by the manufacturer of the scaffold and then provided or sold to an end-user (e.g., a doctor, a veterinarian), or the dissolution step may be performed by an end-user of the scaffold (e.g., a doctor or veterinarian) prior to using the scaffold. The dissolution step may involve immersing, submerging, or otherwise contacting the scaffold with the appropriate solvent (e.g., water). It should be understood that the time and conditions under which the soluble component is dissolved may vary and may be dependent on the particular materials used to fabricate the scaffold. In some cases, the tissue scaffold may be subjected to sonication while immersed in the solvent.

Any number of rapid-prototyping technologies may be utilized to manufacture a three-dimensional tissue scaffold of the disclosure. Non-limiting examples of rapid-prototyping technologies that are suitable may include: stereolithography (SLA), digital light processing (DLP), fused deposition modeling (FDM), selective laser sintering (SLS), selective laser melting (SLM), electron beam melting (EBM), laminated object manufacturing (LOM), bio-plotting, and deposition printing.

In some aspects, the three-dimensional size and shape of a tissue defect may be determined in a subject, prior to fabricating the scaffold. In some cases, the tissue scaffold is manufactured according to the three-dimensional size and shape of a tissue defect. The tissue scaffold may further be manufactured based on the tissue and cell type(s) present at the tissue defect. For example, a tissue defect may involve multiple tissue and cell types, including, for example, bone, cartilage, and vascular tissue. The tissue scaffold may be fabricated according to the unique structure of the tissue defect, such that the tissue scaffold corresponds, at various regions of the scaffold, to the varying tissue and cell types present in the tissue defect. In one aspect, the tissue scaffold may be fabricated to match a porosity and/or density of a corresponding tissue at the defect. In some cases, the tissue scaffold may have a plurality of layers, each of the layers corresponding to a porosity and/or density of a tissue at the defect.

In some aspects, the methods may involve imaging a tissue defect of a subject. For example, a tissue defect may be imaged using one or more medical imaging techniques, such as magnetic resonance imaging (MRI), ultrasound, computed tomography (CT) scanning, X ray radiography, endoscopy, elastography, tactile imaging, thermography, medical photography, positron emission tomography (PET), fluoroscopy, fluorescent based imaging, or single-photon emission computed tomography (SPECT). A data file rendering of the tissue defect (e.g., .stl file) may be produced as described below. Such methods may allow for the design and fabrication of a tissue scaffold that is customized to match the tissue defect.

Additional methods are provided herein for treating a subject having a tissue defect. In some cases, the tissue defect is a large, critical-sized tissue defect. Non-limiting examples of large, critical-sized tissue defects that may be amenable to treatment with the three-dimensional tissue scaffolds of the disclosure may include cosmetic structural, craniofacial, spinal, hip, knee, and small extremity joints (hand, foot, and ankle) defects comprising bone, vasculature, and/or cartilage damage caused by traumatic injury, chronic injury, cancer, or disease. In some aspects, methods for treating a subject having a tissue defect are provided comprising surgically or otherwise implanting a three-dimensional tissue scaffold of the disclosure into a subject having a tissue defect (e.g., at the site of the tissue defect). In some cases, prior to implanting the tissue scaffold into the subject, a three-dimensional shape and/or size of the tissue defect is determined as described above and the tissue scaffold is manufactured based on the dimensions and characteristics of the tissue defect.

The methods may be utilized to treat a subject having a tissue defect, such as a large critical-sized tissue defect. In some cases, the subject is a human. In other cases, the subject is a non-human animal. Non-limiting examples of non-human animals can include a non-human primate, a livestock animal, a domestic pet, and a laboratory animal. For example, a non-human animal can be, an ape (e.g., a chimpanzee, a baboon, a gorilla, or an orangutan), an old world monkey (e.g., a rhesus monkey), a new world monkey, a dog, a cat, a bison, a camel, a banteng, a cow, a deer, a pig, a donkey, a gayal, a horse, a mule, a lama, a sheep, a goat, a buffalo, a reindeer, a yak, a mouse, a rat, a rabbit, or any other non-human animal. In some cases, the animal is an equine (horse or other member of the horse family). In some cases, the horse is a racing horse or a show horse.

The three-dimensional tissue scaffolds of the disclosure may be implanted into a subject by a healthcare provider, such as a surgeon or other medical professional. In situations in which the subject is a non-human animal (e.g., a horse), the tissue scaffold may be implanted into the non-human animal by a veterinarian.

Figure 1B:
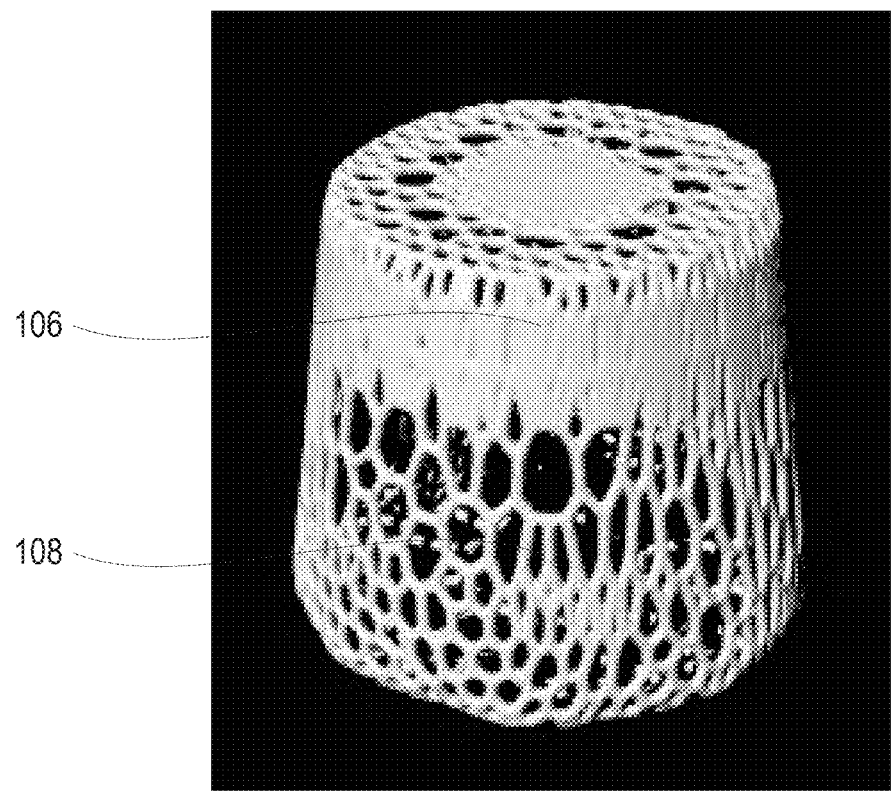
FIG. 1B depicts a perspective view of an exemplary tissue engineering scaffold according to one or more aspects of the present disclosure.
Figure 2:
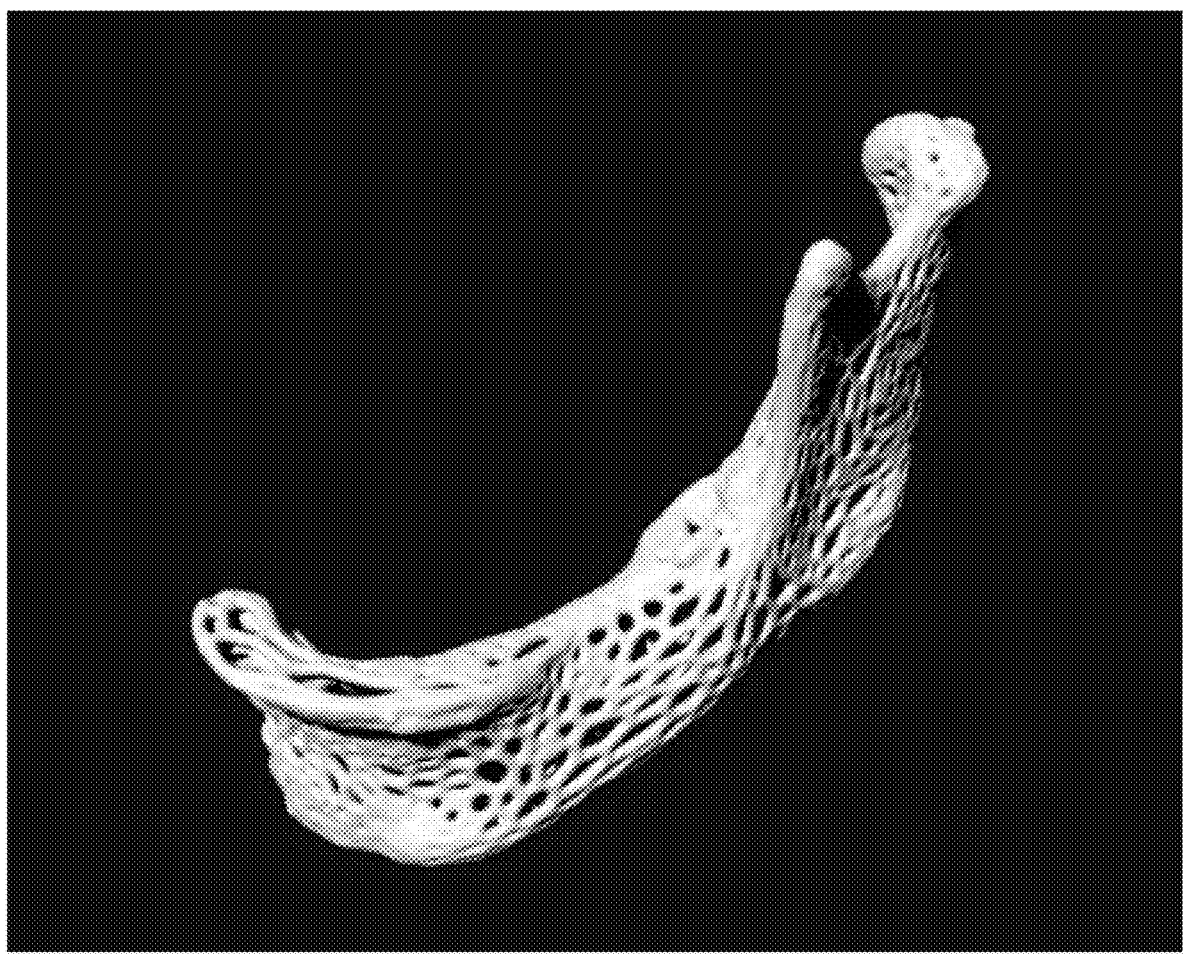
FIG. 2 depicts an exemplary tissue engineering scaffold corresponding to a mandibular defect according to one or more aspects of the present disclosure.

Reference is now made to the drawings and particular aspects of the disclosure. FIGS. 1A and 1B depict a top and perspective view, respectively, of an exemplary tissue engineering scaffold 100 according to one or more illustrative embodiments of the disclosure. The tissue engineering scaffold 100 of FIGS. 1A and 1B is an illustrative and non-limiting example and is exhibited for the purposes of discussing the specificities of the tissue engineering scaffolds contemplated herein. One of ordinary skill in the art will readily appreciate that the specificities discussed below in regards to tissue engineering scaffold 100 may be incorporated into tissue engineering scaffolds corresponding to defects of any of a plurality of dimensions and corresponding to any of a plurality of bone and/or osteochondral areas. For example, as shown in FIG. 2, the tissue engineering scaffold 100 may be formed in the dimensions corresponding to a mandibular defect. Similarly, the tissue engineering scaffold 100 may be formed in the dimensions corresponding to defects of the bones and/or osteochondral areas in the vertebral column, chest, skull, arms, hands, legs, and feet.

The scaffold 100 may be fabricated from a composite material as described herein (e.g., a TPU/water-soluble polyvinyl alcohol (PVA) composite such as Gel-lay). The scaffold may be fabricated via a rapid prototyping technology. Non-limiting examples of a rapid-prototyping technology that may be used to fabricate a tissue scaffold of the disclosure may include: stereolithography (SLA), digital light processing (DLP), fused deposition modeling (FDM), selective laser sintering (SLS), selective laser melting (SLM), electron beam melting (EBM), laminated object manufacturing (LOM), and the like. The TPU/PVA composite may consist of 70 wt % TPU and 30 wt % water-soluble PVA. In some instances, the TPU/PVA composite may consist of alternate TPU and PVA weight percentages ranging from 95 wt % TPU and 5 wt % water-soluble PVA to 50 wt % TPU and 50 wt % water-soluble PVA.

In some instances, the tissue engineering scaffold 100 may be fabricated from polyvinyl alcohol (PVA), polycaprolactone (PCL), or poly lactic acid (PLA) and may be a homogenous construct in regards to the material composition. Alternatively, the tissue engineering scaffold 100 may be produced from a plurality of materials such as, but not limited to, TPU/PVA, PVA, PCL, and PLA and may be a heterogeneous construct. Furthermore, in instances in which the tissue engineering scaffold is a heterogeneous tissue engineering scaffold, the scaffold may be produced from any one, or combination of, rapid prototyping technologies including, but not limited to, SLA, DLP, FDM, SLS, SLM, EBM, and/or LOM. For example, a first portion of the tissue engineering construct may be fabricated from TPU/PVA through SLS, a second portion may be fabricated from PLA through SLA, a third portion may be fabricated from PVA through FDM, and so on.

In instances in which the TPU/PVA composite filament is used, many advantageous structural and mechanical properties may be achieved in the scaffold 100. For example, the TPU composition of the scaffold 100 may exhibit properties including elasticity, strength, flexibility, and biocompatibility. Furthermore, the presence of water-soluble PVA composition may produce a unique stratified micro and/or nanofilamentous structure along the TPU fiber surface of scaffold 100 subsequent to the dissolution of the PVA component after printing. Such a micro and/or nanofilamentous structure may cause the scaffold 100 to retain its shape as originally 3D printed, while also being porous and flexible.

The tissue engineering scaffold 100 may be a three-dimensional construct of any of a plurality of sizes, shapes, porosities, and densities. As stated above, the size and shape of tissue engineering scaffold 100 may correspond to the size and shape of a defect of a bone and/or osteochondral area. Accordingly, the tissue engineering scaffold 100 may be a patient-specific tissue engineering scaffold and may correspond to a defect of a bone and/or osteochondral area particular to a patient.

In some instances, the scaffold 100 may additionally include one or more attachment faces, holes, grooves, protrusions, depressions and the like for adding in the surgical implantation of the scaffold. For example, the scaffold 100 may include a hole configured to receive a screw, wherein the screw is configured to fasten the scaffold to a bone of a patient. Similarly, the scaffold 100 may include a protrusion configured to interface with a surgical clamp thereby facilitating the installation of the scaffold in a patient.

As shown in FIG. 1A, the porosity and density of the scaffold 100 may vary from a center portion of the scaffold to an outer portion. For example, the center portion 102 of scaffold 100 may be of a first porosity and a first density and the outer portion 104 may be of a second porosity greater than the first porosity and a second density less than the first density. Alternatively, the center portion 102 of scaffold 100 may be of a first porosity and a first density and the outer portion 104 may be of a second porosity less than the first porosity and a second density greater than the first density. In some instances, the porosity and density may change linearly from the first porosity and the first density to the second porosity and the second density. In other instances, the porosity and density may change from the first porosity and the first density to the second porosity and the second density without a linear increase or decrease in porosity and density.

As shown in FIG. 1B, the porosity and density of the scaffold 100 may vary from a top portion of the scaffold to a bottom portion. For example, the top portion 106 of scaffold 100 may be of a first porosity and a first density and the bottom portion 108 may be of a second porosity greater than the first porosity and a second density less than the first density. Alternatively, the top portion 106 of scaffold 100 may be of a first porosity and a first density and the bottom portion 108 may be of a second porosity less than the first porosity and a second density greater than the first density. In some instances, the porosity and density may change linearly from the first porosity and the first density to the second porosity and the second density. In other instances, the porosity and density may change from the first porosity and the first density to the second porosity and the second density without a linear increase or decrease in porosity and density.

Similarly, the porosity and density of the scaffold 100 may vary from an interior portion of the scaffold to an exterior portion. For example, the interior portion of scaffold 100 may be of a first porosity and a first density and the outer portion may be of a second porosity greater than the first porosity and a second density less than the first density. Alternatively, the interior portion of scaffold 100 may be of a first porosity and a first density and the outer portion may be of a second porosity less than the first porosity and a second density greater than the first density. In some instances, the porosity and density may change linearly from the first porosity and the first density to the second porosity and the second density. In other instances, the porosity and density may change from the first porosity and the first density to the second porosity and the second density without a linear increase or decrease in porosity and density.

In some instances, the porosity and density of the scaffold 100 may correspond to the porosity and density of the defected area of the particular bone and/or osteochondral area. For example, a scaffold fabricated corresponding to a defect of a particular area of an L3 lumbar vertebrae may be fabricated with the porosity and density of the particular area of the L3 lumbar vertebrae. Similarly, a scaffold fabricated corresponding to a defect of a particular area of a fibula may be fabricated with the porosity and density of the particular area of the fibula. Accordingly, the porosity and density of the scaffold 100 may vary in accordance with the porosity and density of the defected area for which the scaffold is produced. Thus, the scaffold 100 may be of a heterogeneous porosity and density corresponding to that of the particular defected area.

In other instances, the porosity and density of the scaffold 100 may correspond to the porosity and density of the defected area of the particular bone and/or osteochondral area but may be further modulated based on surgical methods needed to install the scaffold and/or surgical procedures needed to create a functional implant. For example, in regards to the mandibular scaffold depicted in FIG. 2, the alveolar process of the mandibular scaffold may be manufactured with increased density and decreased porosity as compared to that of the natural alveolar process in order to accommodate for the surgical installation of prosthetic teeth. Similarly, in instances in which one or more screws and/or pins are needed to install the scaffold, areas of the scaffold around the holes configured to receive the screws and/or pins may be manufactured with a lower porosity and higher density than that of the area of the natural tissue corresponding to the location of the hole on the scaffold.

In any event, the pores of the scaffold 100 may vary between 50 to 300 microns (μm) and may be fabricated in any one, or combination of, a voronoi structure and/or a pre-designed geometric pattern including a plurality of sides and angles. In one example the pores of the scaffold 100 may be square-shaped pores comprising aligned stacked struts which rotate by 90 degrees, hexagon-shaped pores, and/or interconnected horizontal and vertical tubes embedded within solid I fills. As demonstrated herein, all of such topographical structures, porosities, and micro and/or nano-structures have been shown to enhance cartilage, bone, and vascular growth. Additionally, these microstructures can be used in conjunction with each other to encourage multiple, localized, and integrated tissue growth in one implantable device. In particular, the intersecting lines of the voronoi structure may connect at a 60 degree angle conducive for cell adhesion. However, in some instances, the sides of the voronoi structure and/or any of the structures described above may connect at any angle within a range of angles varying between 30 degrees and 120 degrees.

In one instance, the scaffold 100 may include a 'key' structure and/or a veritable pipe or tube structure which, when embedded orthogonal to, but traversing the interface between two disparate microstructures, may increase mechanical strength in compression and shear. Such a 'key' structure is described in PCT Application Serial No. PCT/US2014/029814 entitled "3D Biomimetic, Bi-Phasic, Key Featured Scaffold for Osteochondral Repair," which was filed on Mar. 14, 2015 and was also described in U.S. application Ser. No. 14/854,584 entitled "3D Biomimetic, Bi-Phasic, Key Featured Scaffold for Osteochondral Repair," which was filed on Sep. 15, 2015.

As stated above, the scaffold 100 may be manufactured from a plurality of materials through a plurality of manufacturing processes. For example, a top, center, and/or inner portion of scaffold 100 may be manufactured from a first material (e.g., TPU/PVA) through a first manufacturing process (e.g., selective laser sintering) and a bottom, outer, and/or external portion of the scaffold may be manufactured from a second material (e.g., PLA) through a second manufacturing process (e.g., fused deposition modeling). In some instances, the scaffold 100 may be manufactured from a plurality of materials through a single manufacturing process.

The selection of materials for the production of scaffold 100 may depend on the type of defect and the mechanical properties required to be replicated by the scaffold. For example, in the event that a patient has a knee cartilage defect and has microfracture surgery to facilitate cartilage regeneration in the defected area, a scaffold 100 may be fabricated with a first material configured to cap and/or plug bone punctures created by the microfracture surgery and a second material configured to replicate defected area of cartilage. Accordingly, the first material may be required to be a more flexible material (e.g., PLA) and may be required to be fabricated with a high porosity and low density to allow for the expulsion of blood and bone marrow and the second material may be a required to be a more rigid material (e.g., TPU/PVA) and may be required to be fabricated with a low porosity and high density in order to replicate the mechanical properties of cartilage.

Figure 3:
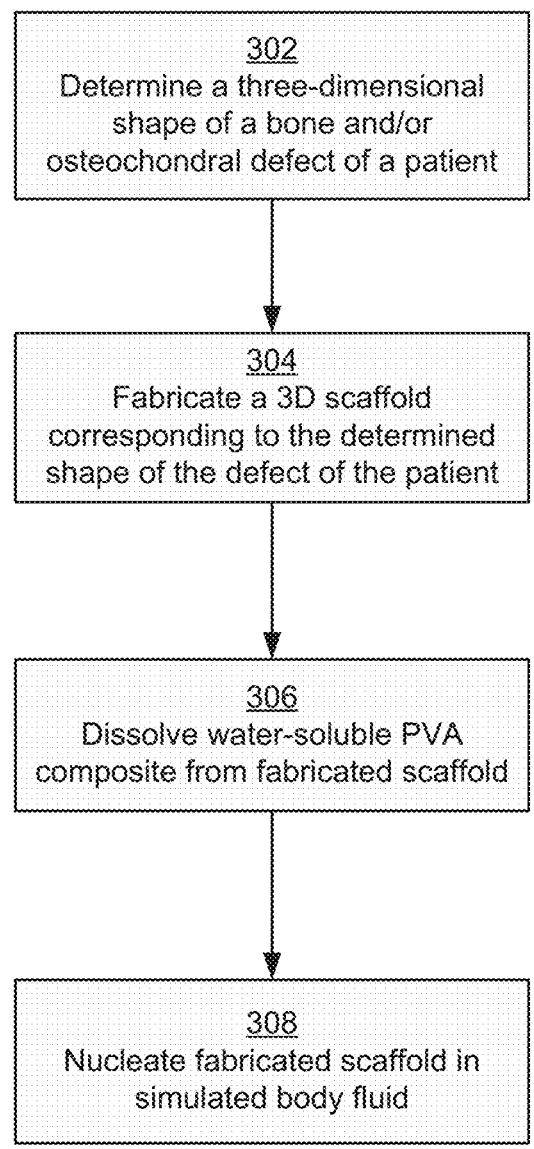
FIG. 3 is a flow diagram illustrating an example method of fabricating a tissue engineering scaffold according to one or more aspects of the disclosure.

FIG. 3 is a flow diagram illustrating an example method of fabricating a tissue engineering scaffold according to one or more aspects of the disclosure. At step 302, a three-dimensional shape of a bone and/or osteochondral defect of a patient may be determined. In some instances, the three-dimensional shape of the defect may be determined through the performance of a magnetic resonance imaging scan (MRI scan) and/or computed tomography scan (CT scan) of the area of the patient corresponding to the defect.

After the MRI and/or CT scan has been performed, the MRI and/or CT scan data may be analyzed to create a .stl file rendering of the defected area. In some instances, after the .stl file has been generated, the file may be further treated to vary the porosity and/or density of construct and to create any attachment faces, holes, grooves, protrusions, depressions and the like for adding in the surgical implantation of the scaffold. Additionally, the file may be treated to demarcate areas of the construct to be fabricated from a specific material and/or a specific rapid prototyping method. For example, a first portion of the construct may be marked to be fabricated from TPU/PVA through SLS and a second portion of the construct may be marked to be fabricated from PLA through FDM. Responsive to rendering and treating the .stl file, the file may be further processed in order to produce a version of the file in a numerical control programming language (e.g., G-code) that can be read by the one or more rapid prototyping machines to be used in the fabrication of tissue engineering scaffold associated with the .stl file.

At step 304, a 3D tissue engineering scaffold may be fabricated corresponding to the determined three-dimensional shape of the bone and/or osteochondral defect of the patient via one or more rapid prototyping machines. Depending on the extent of the treatment to the .stl file, the fabricated 3D tissue engineering scaffold may be manufactured from one or more materials (e.g., TPU/PVA, PVA, PCL, and/or PLA) via one or more rapid prototyping machines (e.g., SLA, DLP, FDM, SLS, SLM, EBM, and/or LOM).

At step 306, in instances in which TPU/PVA was used in the manufacture of at least a portion of the fabricated 3D tissue engineering scaffold, the PVA composite of the TPU/PVA material may be dissolved from the fabricated scaffold. In one instance, the dissolution of the PVA composite may be performed by immersing the fabricated scaffold in ultrapure water. In another instance, the dissolution of the PVA composite of the TPU/PVA material may be performed by immersing the fabricated scaffold in ultrapure water and ultrasonicating fabricated scaffold immersed in the ultrapure water.

At step 308, after the PVA component has been dissolved from the fabricated tissue engineering scaffold, the scaffold may be nucleated in simulated body fluid. In some instances, the nucleation in simulated body fluid may be performed for any period less than or equal to two months. Additionally, the fabricated tissue engineering scaffold may be further processed through vascular endothelial growth factor treatments, selenium treatments, germicidal nanoparticle treatments, and/or silver nanoparticle treatments.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

In one example, tissue engineering scaffolds fabricated from bioactive and biomimetic thermoplastic polymer composite materials were designed for bone, vascular, and cartilage regeneration. The tissue engineering scaffolds were fabricated as patient-specific tissue engineering scaffolds and, as such, were manufactured in accordance with the three-dimensional shape of bone, vascular, and cartilage defects of a patient. The tissue engineering scaffolds were fabricated using industrial quality, high throughput 3D printing methods for causing tissue repair leading to functional recovery.

In particular, the tissue engineering scaffolds were fabricated through any one, or combination of, selective laser sintering (SLS), stereolithography (SLA), and fused-deposition modeling (FDM) methods. The 3D printed tissue engineering scaffolds comprise a first region of a first porosity and a first density and a second region of a second porosity and a second density. The first region may correspond to a bone region and the second region may correspond to a cartilage region. In some instances, the first porosity may be greater than the second porosity and the first density may be less than the second density. Alternatively, the first porosity may be less than the second porosity and the first density may be greater than the second density.

The fabricated tissue engineering scaffolds were designed with varying micro-porosity and material pattern in order to improve bone, vascular, and cartilage formation and to promote bone, vascular, and cartilage in-growth in appropriate and specified locations to create mechanical and blood flow properties similar to that of native tissue. In particular, the tissue engineering scaffolds were designed with a varying porosity and nano hydroxyapatite (nHA) content. Additionally, the scaffolds were designed to include bone micro patterns with designed, blood vessel like microchannels. Such a design may be employed to replicate the structure of subchondral bone, the transitional zone between subchondral bone and articulate cartilage, and articulate cartilage. Accordingly, the 3D printed tissue engineering scaffold may be able to both support mechanical loading similar to native bone and cartilage, and to promote fast and efficient fluid perfusion, namely of arterial blood, throughout the scaffold. This is especially important for initial induction of progenitor cells and early vascular formation deep within the implant microarchitecture.

The tissue engineering scaffolds described above were manufactured from any one, or combination of, powderized TPU/PVA composite (e.g., Gel-lay), polyvinyl alcohol (PVA), polycaprolactone (PCL), and poly lactic acid (PLA). Accordingly, the first region of the tissue engineering scaffold may be fabricated from a first material (e.g., PLA) through a first 3D printing process (e.g., FDM) and the second region may be fabricated from a second material (e.g., Gel-lay) through a second 3D printing process (e.g., SLS). However, in some instances, the first and second regions may be fabricated from the same material through the same 3D printing process.

In regards to the 3D printed tissue engineering scaffolds wherein at least one of the first and second regions were manufactured from the powderized TPU/PVA composite, many advantageous qualities were observed. For instance, in the presence of water the PVA dissolves, leaving only the soft TPU material. The TPU material when left becomes highly elastic, yet strong, and acquires an aligned nonporous topography. Such qualities, combined with the 3D printed microporous structure, create a hierarchical micro to nano porosity, which has been shown to be ideal for stem cell recruitment, growth, and differentiation and, thus, for accelerating the formation of new bone, cartilage, and vascular networks. Furthermore, the TPU component of the Gel-lay material also has physical characteristics and compressive and elastic properties similar to native tissues at the osteochondral region. Accordingly, the 3D printed tissue engineering scaffolds manufactured at least in part from the powderized TPU/PVA composite may form a transitional structure which looks like osteochondral tissue, replaces the function of lost cartilage, and causes new vascularized subchondral bone to form in the scaffold anchoring it permanently in place and repairing the articular surface when implanted in the patient.

After fabrication and in instances in which the powderized TPU/PVA composite was used in the manufacture of the tissue engineering scaffolds, the scaffolds were immersed in ultrapure water and ultrasonicated at 60° C. for three 90 minute cycles. This process was used to fully dissolve the PVA component of manufactured tissue engineering scaffold. Subsequently, the scaffolds were sterilized via Ethylene Oxide (EtO) in a sterilizer to ensure that no morphological changes were to occur.

The scaffolds were then evaluated via scanning electron microscopy (SEM) at an accelerating voltage of 1.5 kV to assess the degree of PVA dissolution and development of the nanoporous structure throughout the TPU. Prior to SEM analysis, the 3D printed scaffolds were air dried overnight and gold sputter-coated.

The compressive modulus of the 3D printed tissue engineering scaffolds was determined via uniaxial compression testing fitted with a 1 kN load cell at a crosshead speed of 5 mm/min. Additionally, shear testing was conducted to quantify the integrity of the bone-cartilage interface. Load and displacement were used to plot the stress-strain curves and the Young's modulus was calculated from the linear elastic region. Surface charge of the scaffold was measured by drop shape analysis using a contact angle analyzer.

Next, the industrial capability of the 3D printed tissue engineering scaffolds was determined via evaluation of human mesenchymal stem cells (hMSCs) and endothelial cell cytocompatibility for physically and chemically enhanced long-term osteochondral regeneration. In particular, there were three main experimental groups: plain scaffolds, scaffolds with the bone region nucleated in simulated body fluid, and scaffolds nucleated in simulated body fluid and VEGF. Primary mesenchymal stem cells (MSCs) were obtained from healthy consenting donor's iliac crest and endothelial cells were obtained from a consenting donor's umbilical vein (e.g., HUVECs).

Briefly, the cells were expanded in their respective media under standard cell culture conditions of 37° C., and a 5% CO2/95% humidified air environment. Samples were pre-wetted with a 50:50 mix of complete cell media and endothelial growth media, overnight. The 3D printed tissue engineering scaffolds were seeded with MSCs and HUVECs pre-labeled with wheat germ agglutinin (WGA) labeled with Texas Red (TX-Red) or Green Fluorescent Protein (GFP). At predetermined time points, 4 hours, 1, 3, and 5 days the scaffolds were rinsed with phosphate-buffered saline (PBS) and fixed in 10% Formalin for 20 minutes, rinsed 3× with PBS, and permeabilized with 10% Triton-X for 5 minutes. Fixed samples were double-stained with Texas Red-Phalloidin® (cytoskeleton) for 20 minutes, rinsed 3× with PBS followed by staining for 5 minutes with 4',6-diamidino-2-phenylindole (DAPI). Samples were imaged via confocal microscopy. Additional samples were cultured with non-labeled MSCs and HUVECs, in the manner described, and imaged at 1 and 2 weeks. Samples were fixed in formalin and stained for osteopontin and Von willebrand factor, to detect early signs of bone and vascular formation.

Figures 4A, 4B:
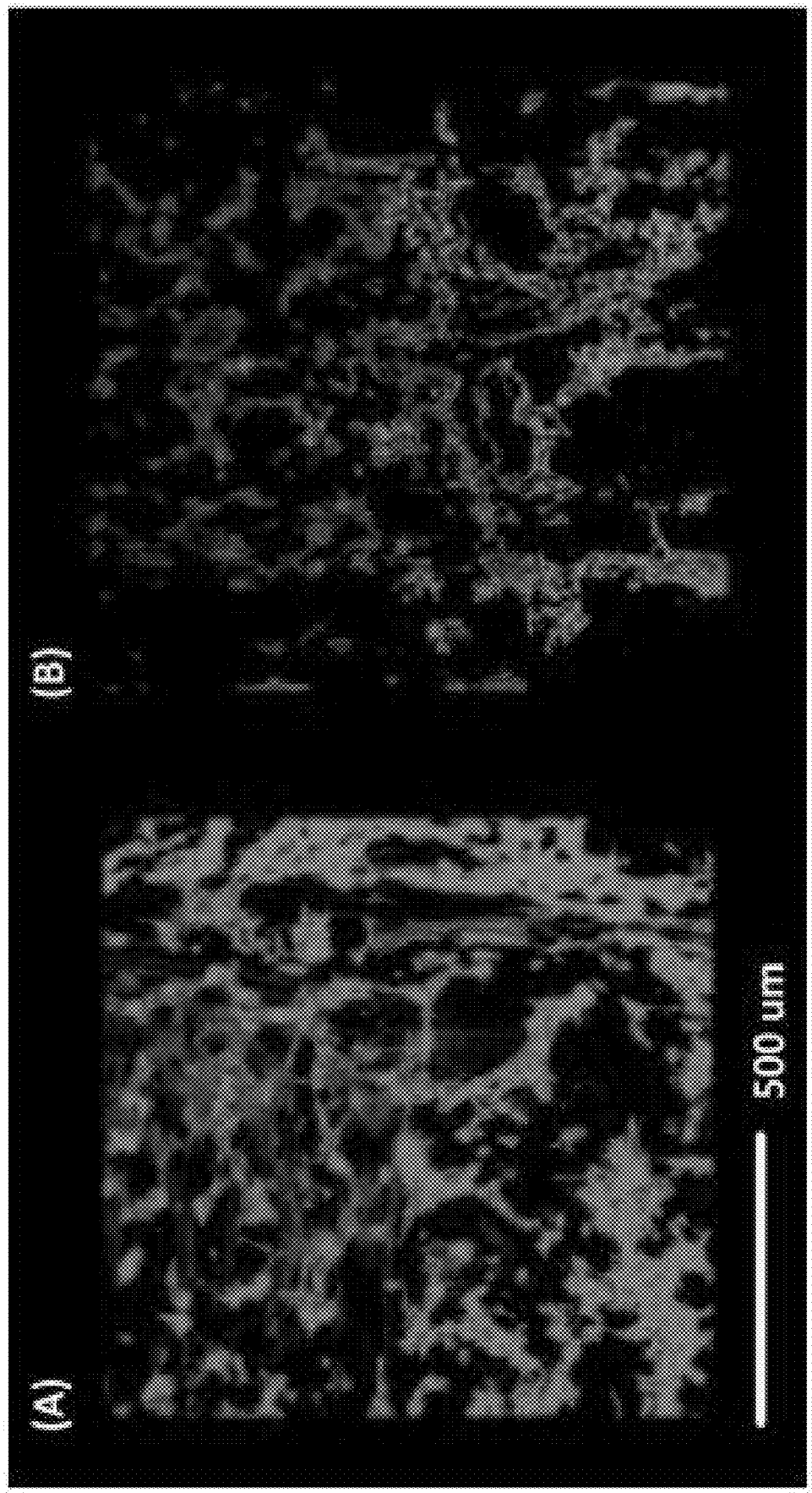
FIG. 4A & FIG. 4B depict confocal microscopy images of human umbilical vein endothelial cellular networks on a 3D printed thermoplastic polyurethane (TPU) scaffolds according to one or more aspects of the disclosure.

FIG. 4A & FIG. 4B show an image of a 3D printed TPU scaffold cultured with HUVECs (e.g., image A) and an image of a 3D printed TPU scaffold modified with angiogenic factors and cultured with HUVECs (e.g., image B). After one day, cells can be seen forming dense cellular networks indicative of vasculature in both images A and B. Treatment with human derived vascular endothelial growth factor (VEGF) 121 and angiogenic amphiphilic peptide nanomaterial further improved performance (e.g., image B). Samples were also treated in simulated body fluid at 37° C., demonstrating the ability of TPU scaffolds to absorb calcium and other ions from the surrounding environment.

Example 2

In another example, tissue engineering scaffolds comprising a solid bottom and porous interconnecting fiber structure were designed in computer-aided design software (e.g., CAD software) and the resulting .stl files were prepared for 3D printing by conversion to a computer numerical control file (e.g., G-code) with the open source software package Slic3r. Next, the models were printed using a Solidoodle© table-top fused deposition modeling printer with Gel-Lay porous 3D printing filament.

Subsequent to fabrication, the 3D printed TPU/PVA composite scaffolds were immersed in ultrapure water and ultrasonicated at 60° C. for three 90 minute cycles to fully dissolve the PVA component. The scaffolds were then washed with distilled water, air-dried at room temperature, and were subjected to scaffolds were subjected to hydroxyapatite nucleation by submersion in simulated body fluid (SBF). The SBF was prepared with 700 mL of ion-exchanged distilled water, 8.035 g NaCl, 0.355 g NaHCO3, 0.225 g KCl, 0.231 g K2HPO4.3H2O, 0.311 g MgCl2.6H2O, 39 mL 1.0M-HCl, 0.292 g CaCl2, 0.072 g Na2SO4, 6.118 g Tris with a pH of 7.42±0.0.1 in a polypropylene beaker with a magnetic stir bar at 36.5±1.5° C. The 3D printed scaffolds were soaked in the SBF for 24, 72 and 120 hour nucleation times. The nucleated scaffolds were then removed, blotted dry, and air-dried. Nucleated and non-nucleated scaffolds were trimmed, placed in cell culture plates, and sterilized under ultraviolet light prior to cell studies.

Figure 5A:
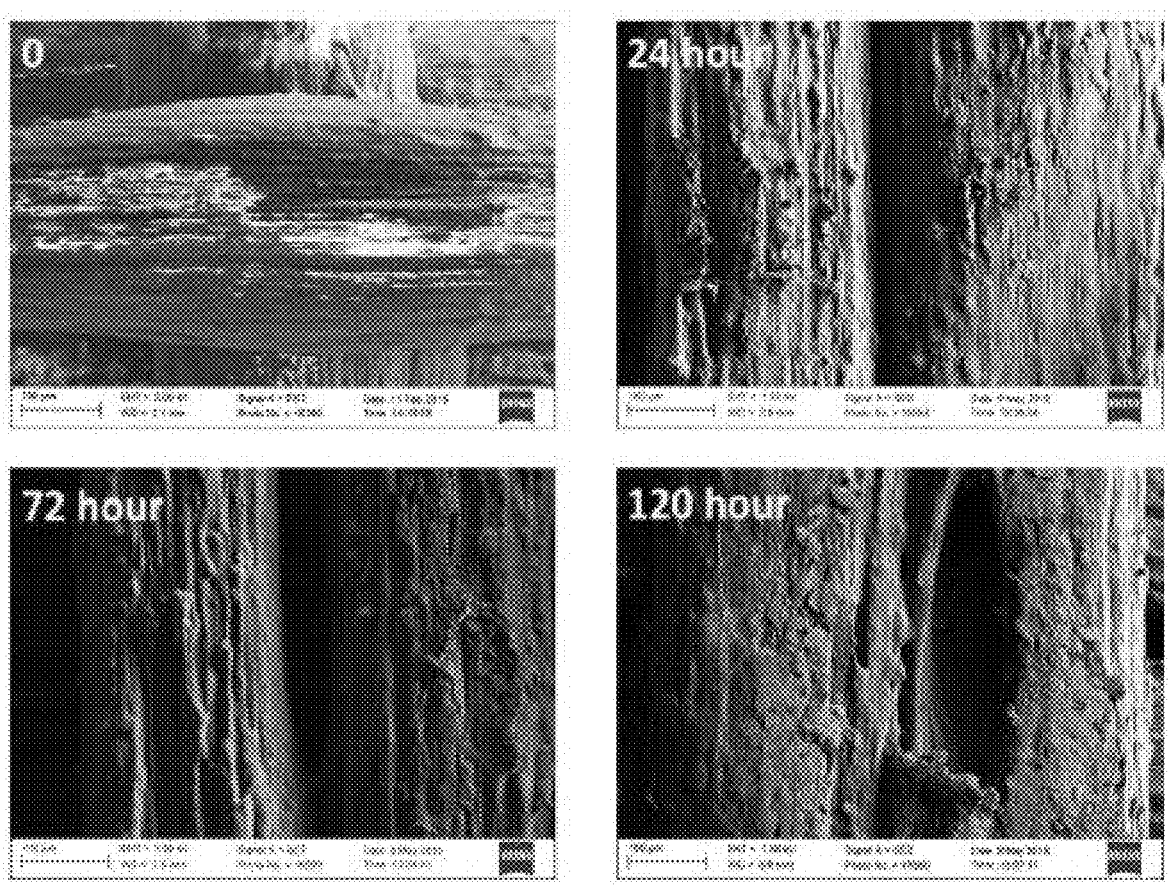
FIG. 5A depicts scanning electron microscopy (SEM) images of nucleated 3D printed TPU scaffolds after various simulated body fluid (SBF) incubation periods according to one or more aspects of the disclosure.
Figure 5B:
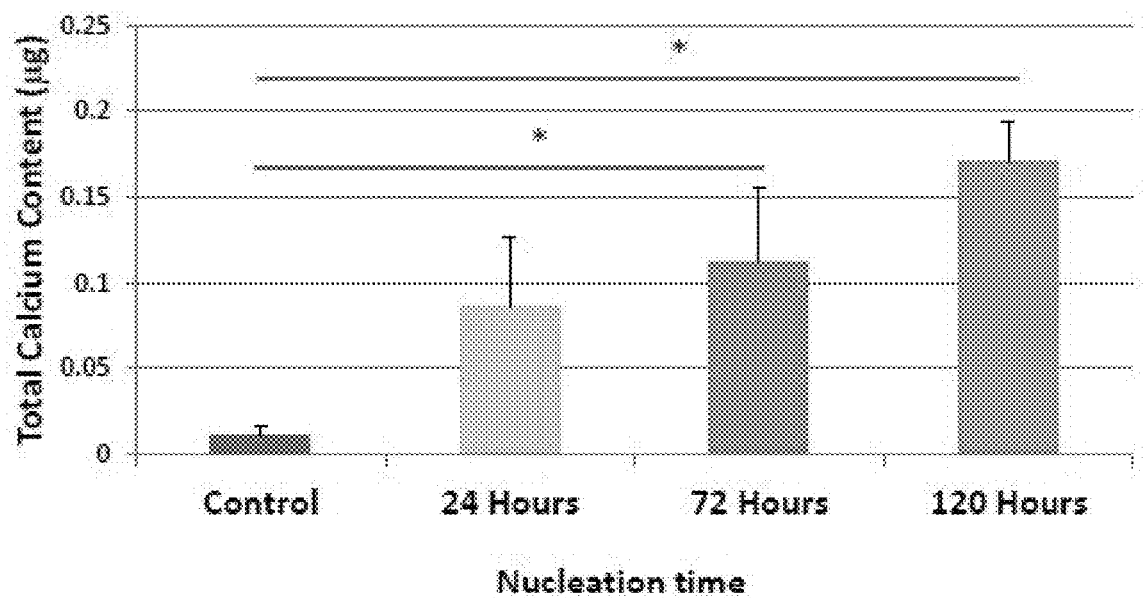
FIG. 5B depicts a graph of the total nucleated calcium content in micrograms (μg) of the control and nucleated 3D printed TPU scaffolds as a function of nucleation periods according to one or more aspects of the disclosure.
Figure 6:
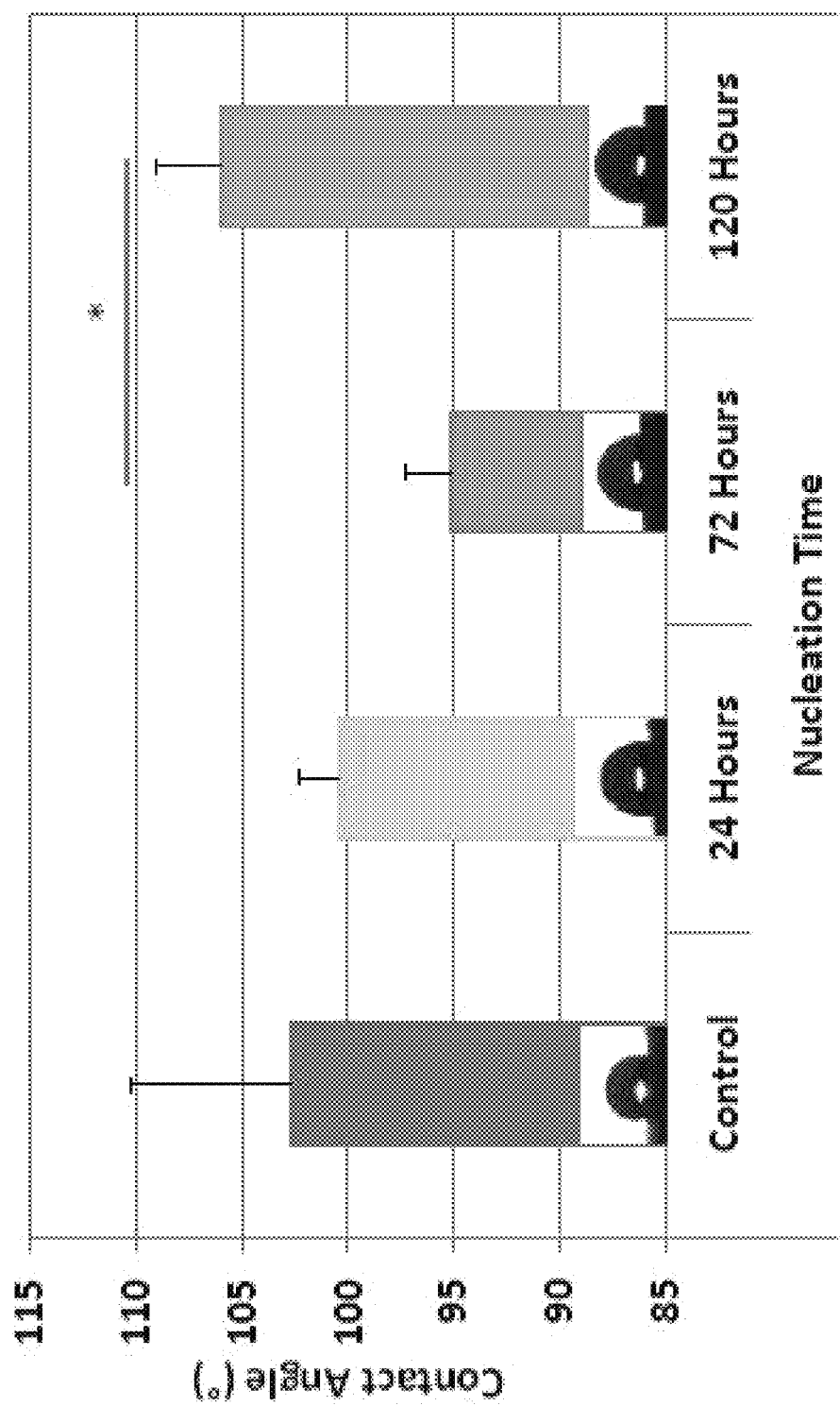
FIG. 6 depicts a graph of the contact angle analysis of the control and SBF nucleated 3D printed TPU scaffolds at a plurality of nucleation times according to one or more aspects of the disclosure.
Figure 7:
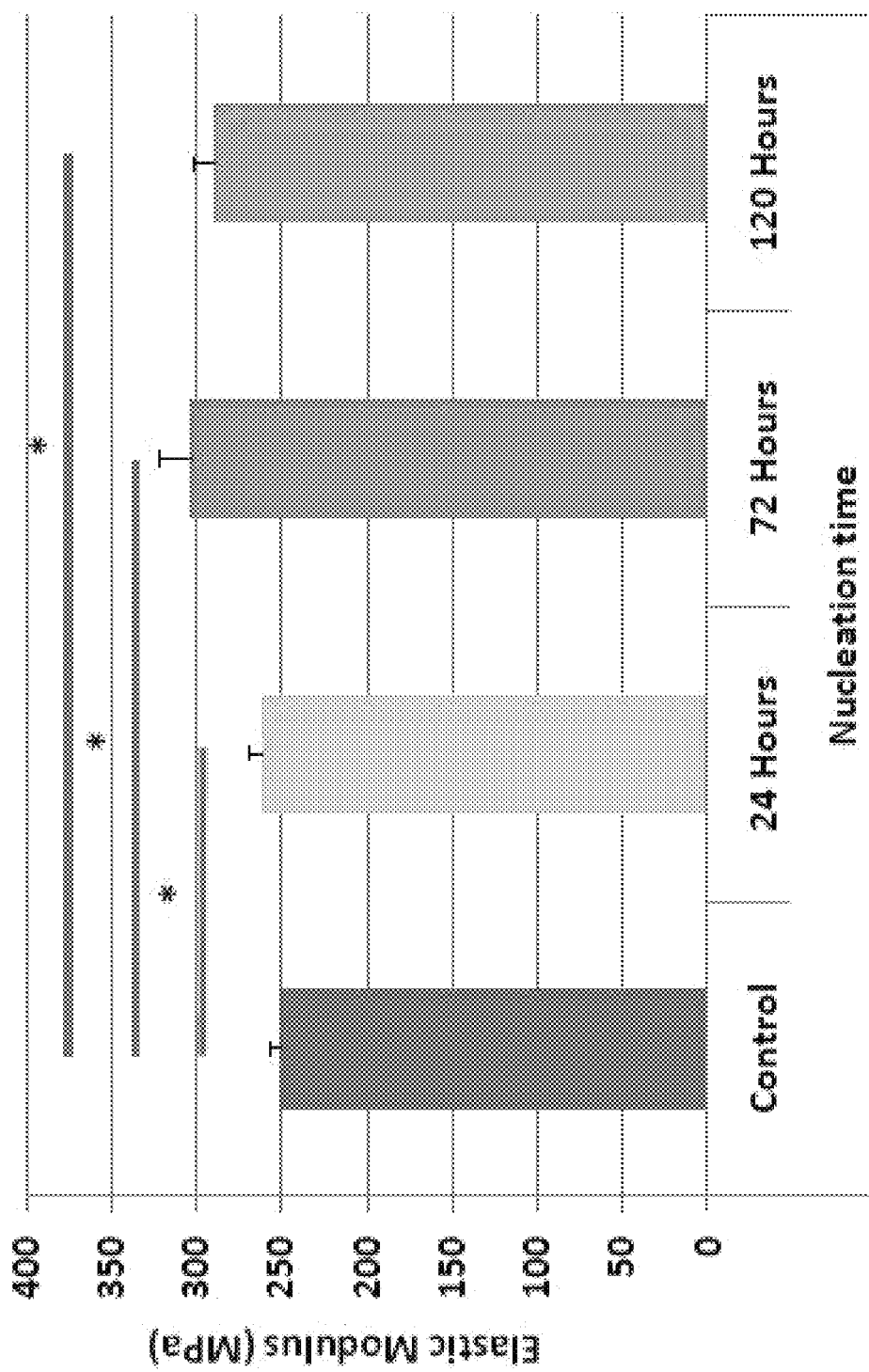
FIG. 7 depicts a graph of the elastic modulus in megapascals (MPa) of the control and SBF nucleated 3D printed TPU scaffolds at a plurality of nucleation times according to one or more aspects of the disclosure.

Responsive to the completion of the nucleation and cell study preparation, the nucleated and non-nucleated scaffolds were air dried overnight and gold sputter-coated prior to scanning electron microscopy (SEM) analysis at an accelerating voltage of 1.5 kV. The compressive modulus of nucleated and non-nucleated 3D printed TPU scaffolds was determined via uniaxial compression testing fitted with a 1 kN load cell at a crosshead speed of 5 mm/min. FIG. 5A depicts scaffold morphology and nucleation and corresponding data quantifying nucleated Ca2+ as a function of incubation time is shown in FIG. 5B. As shown in FIG. 6, surface charge of the scaffold was measured by drop shape analysis using a contact angle analyzer. Load and displacement were used to plot the stress-strain curves and the Young's modulus was calculated from the linear elastic region as shown in FIG. 7.

Human fetal osteoblasts (e.g., CRL-11372) were cultured in Dulbecco's Modified Eagle's Medium and supplemented with 10% fetal bovine serum (FBS) and 1% penicillin/streptomycin (Hyclone) under standard cell culture conditions of 37° C., and a 5% CO2/95% humidified air environment. For human fetal osteoblasts (hFOB) adhesion and proliferation, scaffolds were placed in cell culture plates and sterilized under UV light. The sterilized samples were pre-wetted with media overnight. A density of 50,000 cells/scaffold and 10,000 cells/scaffold were used for cell adhesion and proliferation experiments, respectively. At predetermined time points (e.g., 4 hours, 1, 3, and 5 days), the scaffolds were rinsed with phosphate-buffered saline (PBS) and the adherent cells were enzymatically lifted with 0.25%

Figure 8:
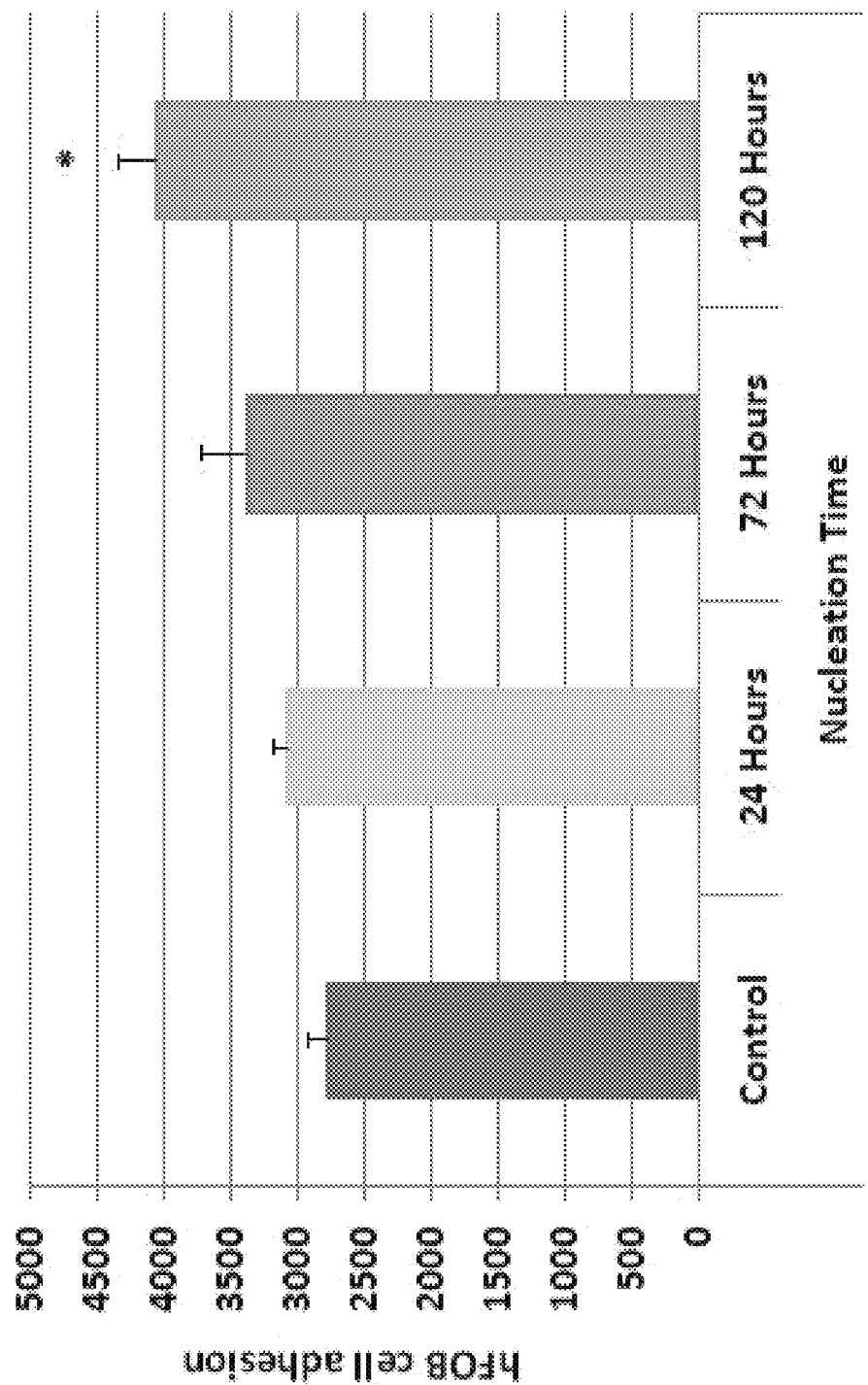
FIG. 8 depicts a graph of the human fetal osteoblastic (hFOB) cell adhesion numbers on the control and SBF nucleated 3D printed TPU scaffolds at a plurality of nucleation times according to one or more aspects of the disclosure.

Trypsin-EDTA. A 100 µL aliquot of cell suspension was transferred to a fresh cell culture plates and 20 µL of CellTiter 96® AQueous Non-Radioactive Cell Proliferation Assay solution was added. The well plate was incubated for 1 hour then read spectrophotometrically at 490 nm. As shown in FIG. 8, a 10%, 17% and 31% increase in hFOB adhesion was observed after 24, 72 and 120 hour nucleation, respectively.

Figure 9:
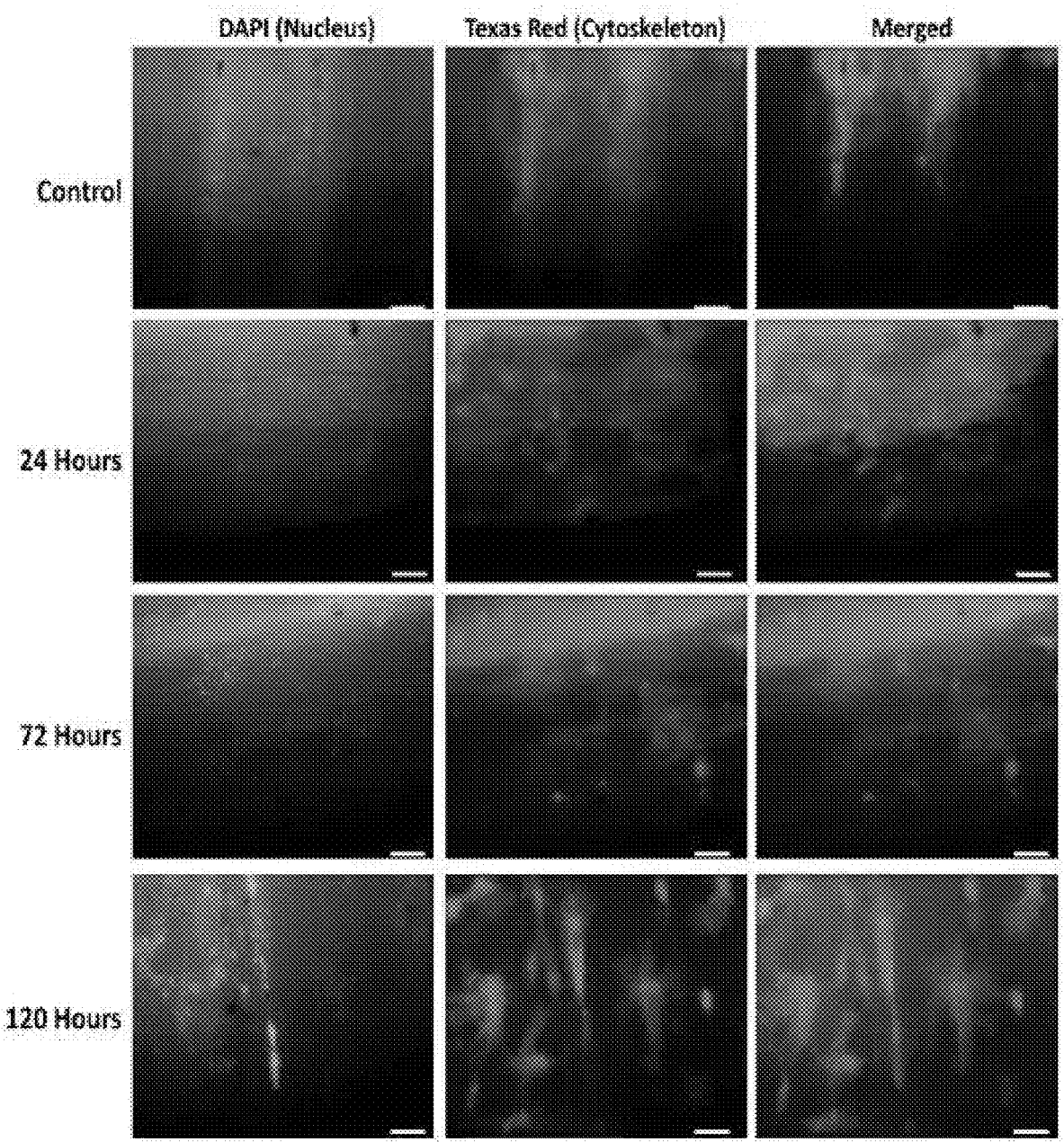
FIG. 9 depicts fluorescence microscopy images of the hFOB cell growth on the control and SBF nucleated 3D printed TPU scaffolds at a plurality of nucleation times according to one or more aspects of the disclosure.

One scaffold from each nucleation time group was fixed in 10% Formalin for 20 minutes, rinsed three times with PBS, and permeabilized with 10% Triton-X for 5 minutes. Fixed samples were double-stained with Texas Red-Phalloidin® (cytoskeleton) for 20 minutes, rinsed three times with PBS followed by staining for 5 minutes with 4',6-diamidino-2-phenylindole (DAPI). Samples were imaged with a 10× objective. As shown in FIG. 9, fluorescence microscopy analysis revealed excellent cell attachment and spreading after 24 hours of culture with a high concentration of cell spreading amongst nucleated samples groups.

For osteogenesis studies, hFOBs were seeded at a density of 10,0000 cells/scaffold on non-nucleated, 24 hour, 72 hour, and 120 hour nucleated scaffolds in a 96-well cell culture plate. After 24 hours, scaffolds were transferred to 48-well plate and cultured in osteogenic media consisting of DMEM media supplemented 10% FBS, 1% penicillin/streptomycin, 50 µg/mL L-ascorbic acid, and 10 mM β-glycerophosphate for 1, 2, and 3 weeks under standard cell culture conditions. Osteoblasts were lysed using distilled water and three freeze-thaw cycles to remove intracellular and membrane-bound proteins. All lysed samples were stored at −80° C. All biochemical analyses were normalized to cell number with results given as units per cell.

Figure 10:
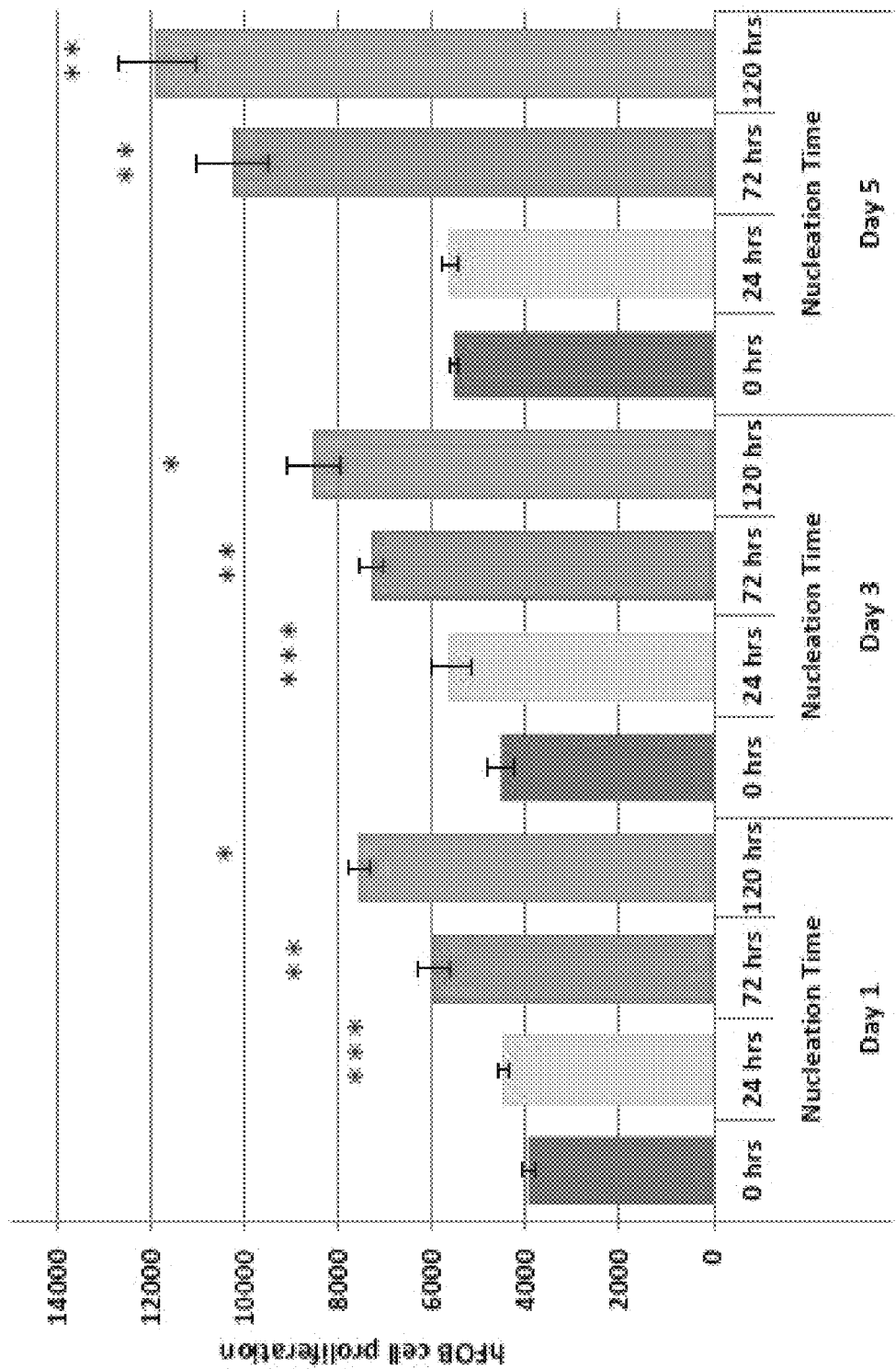
FIG. 10 depicts a graph of hFOB cell proliferation numbers on the control and SBF nucleated 3D printed TPU scaffolds at a plurality of nucleation times after a first, third, and fifth day according to one or more aspects of the disclosure.

As shown in FIG. 10, all nucleated sample groups showed increased cell proliferation after 1, 3 and 5 days with 72 and 120 hour nucleated samples exhibiting a >30% and >40% increase after 1 and 3 days, respectively. After 5 days of culture, a more pronounced increase in cell proliferation was seen with an increase of 46% and 53% for 72 and 120 hour nucleation, respectively. Based on these initial findings, 120 hour nucleated TPU scaffolds were evaluated for three-week hFOB osteogenesis.

Total DNA content was determined to directly quantify total cell number for all differentiation biochemical assays. In short, a 1:100 mixture of Quant-iT™ PicoGreen® dsDNA Reagent in 1× Tris-EDTA (TE) buffer (10 mM Tris-HCl, 1 mM EDTA, pH 7.5) and lysed sample was added to a 96-well plate and read after 5 minute incubation at room temperature with an excitation wavelength of 485 nm and an emission wavelength of 528 nm.

The alkaline phosphatase activity in the cell lysates prepared above was evaluated by a commercially available Alkaline/Acid Phosphatase Assay kit. For this purpose, 20 µL of cell lysate was mixed with 5 µL NiCl2, 5 µL bovine serum albumin (BSA) and 5 µL phosphopeptide stock solution and 45 µL pNPP ser/thr assay buffer in one well of a 96-well microplate. Then, 25 µL aliquots of above mixtures (in triplicate) were transferred into a new plate and were incubated for 15 min at 37° C. 100 µL of Malachite Green solution was added to detect alkaline phosphatase activity. The absorbance of the prepared samples was read on a spectrophotometer at an absorbance wavelength of 650 nm. Alkaline phosphatase synthesized by osteoblasts cultured on the substrates of interest to this study was calculated according a standard curve of known concentrations of phosphate versus absorbance run in parallel with the experimental samples.

Figure 11:
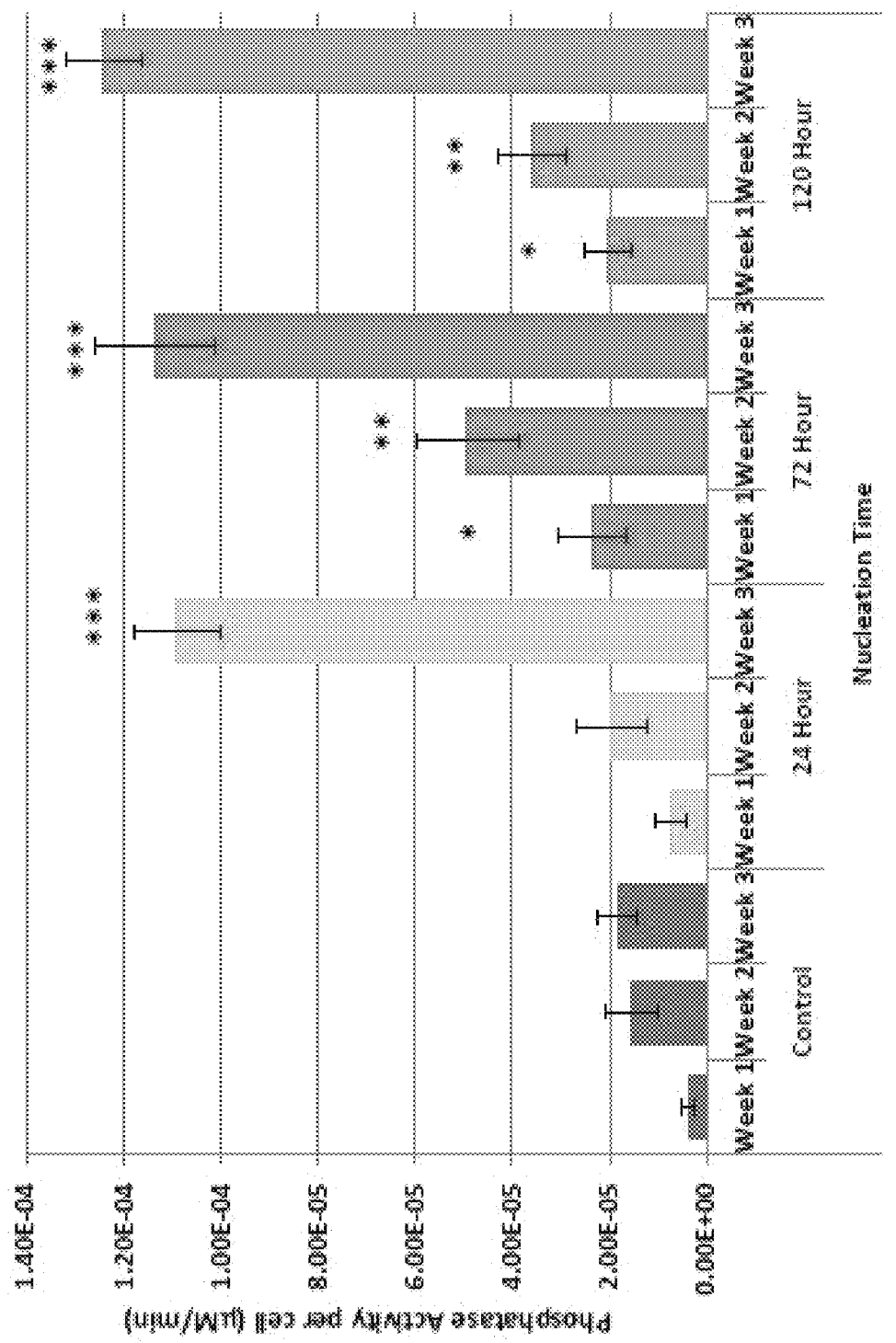
FIG. 11 depicts a graph of the alkaline phosphatase activity per cell in micrometers (μm) per minute of the control and SBF nucleated 3D printed TPU scaffolds at a plurality of nucleation times after a first, second, and third week according to one or more aspects of the disclosure.

As shown in FIG. 11, after one-week of culture, 72 and 120 hour nucleated samples showed a significant increase, 533% and 443%, respectively, in ALP activity when compared to 24 hour and non-nucleated control. After two weeks, 72 and 120 hour nucleated samples maintained increased ALP activity with a 219% and 134% increase over 24 hour and non-nucleated control, respectively. All nucleated samples showed a dramatic increase in ALP activity after three weeks with a more than 5-fold increase over control. These results show the effectiveness of SBF nucleation in osteoinduction.

Calcium deposition was measured using a calcium reagent kit. Briefly, after osteoblasts were lysed, the scaffolds were immersed in a 0.6 N HCl solution at 37° C. for 24 hours. After the prescribed time period, the amount of dissolved calcium present in the acidic supernatant was measured by reacting with the o-cresolphthalein complexone to form a purple-color solution. The light absorbance of these samples was measured at 570 nm spectrophotometrically. Total calcium deposition was calculated from standard curves of known calcium concentrations versus absorbance run in parallel with the experimental samples. Calcium deposition values were normalized to remove the contribution of nucleation and expressed as total mass.

Figure 12:
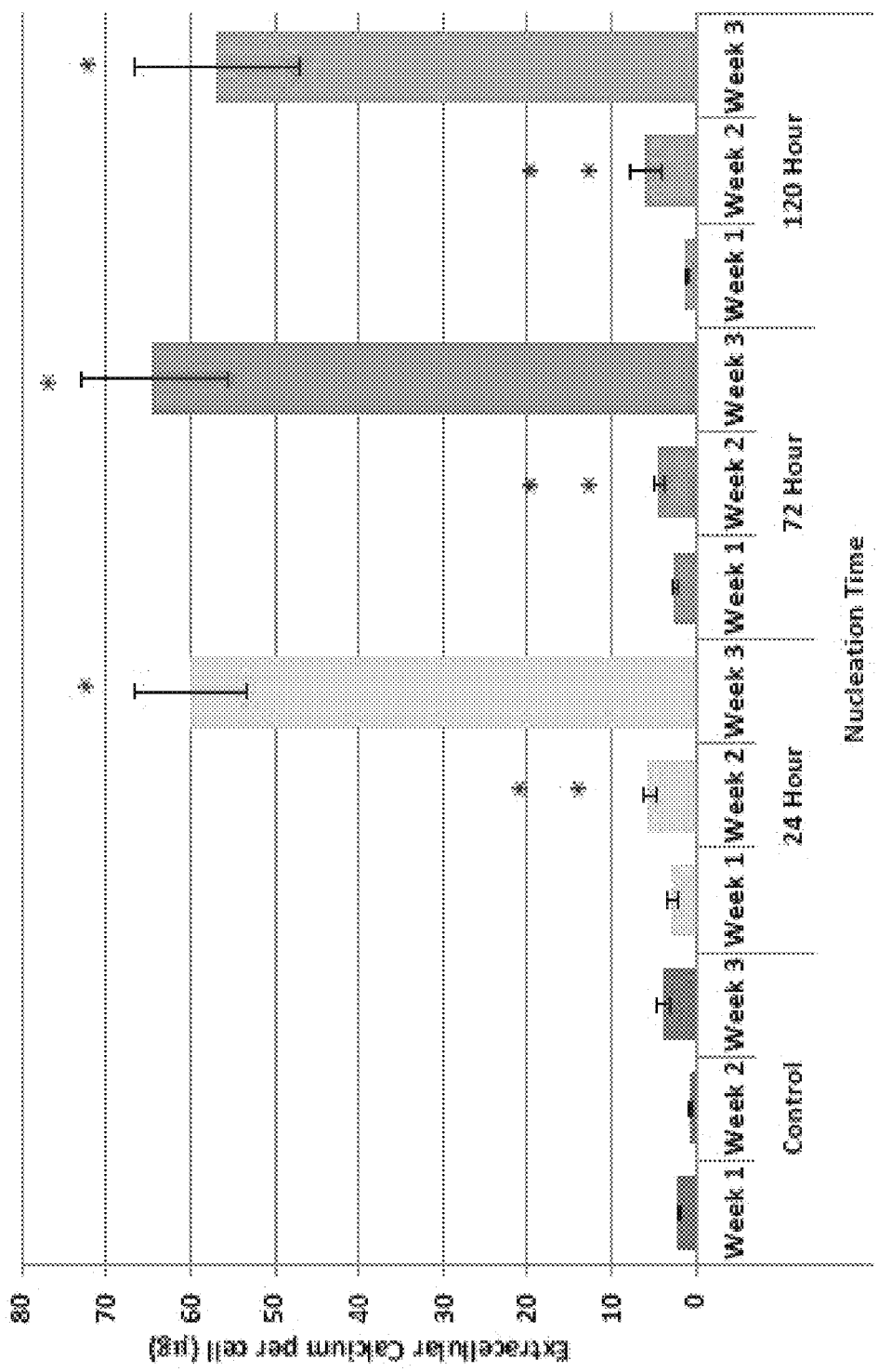
FIG. 12 depicts a graph of the total extracellular calcium deposition content in micrograms (μg) per cell of the control and nucleated 3D printed TPU scaffolds at a plurality of nucleation times after a first, second, and third week according to one or more aspects of the disclosure.

As shown in FIG. 12, all nucleated samples showed a similar trend to ALP activity with a significant increase in extracellular calcium deposition when compared non-nucleated control after two and three weeks. After two weeks, all nucleated samples exhibited a >5-fold increased and after three weeks a greater than 14-fold increase when compared to non-nucleated control. These results further demonstrate that calcium deposition on 3D printed bioactive scaffolds can be further enhanced by SBF nucleation.

The total collagen content of lysed samples was evaluated via Sircol collagen assay kit (Accurate Chemical & Scientific Corp., Westbury, N.Y.). A 100 µL aliquot of each lysate was added to a 96-well plate and dried overnight on a hotplate at 60° C. 150 µL of 0.1% Sirius Red in saturated Picric Acid was added to each dried lysate sample and incubated for 1 hour at room temperature. The samples were then washed four times with 5% acetic acid and then incubated in 0.1 M NaOH for 30 minutes. A 100 µL aliquot of each sample was transferred to a new 96-well plate and a measurement was taken at 555 nm and total collagen per cell was calculated based on a pre-made standard curve with known concentrations of collagen.

Figure 13:
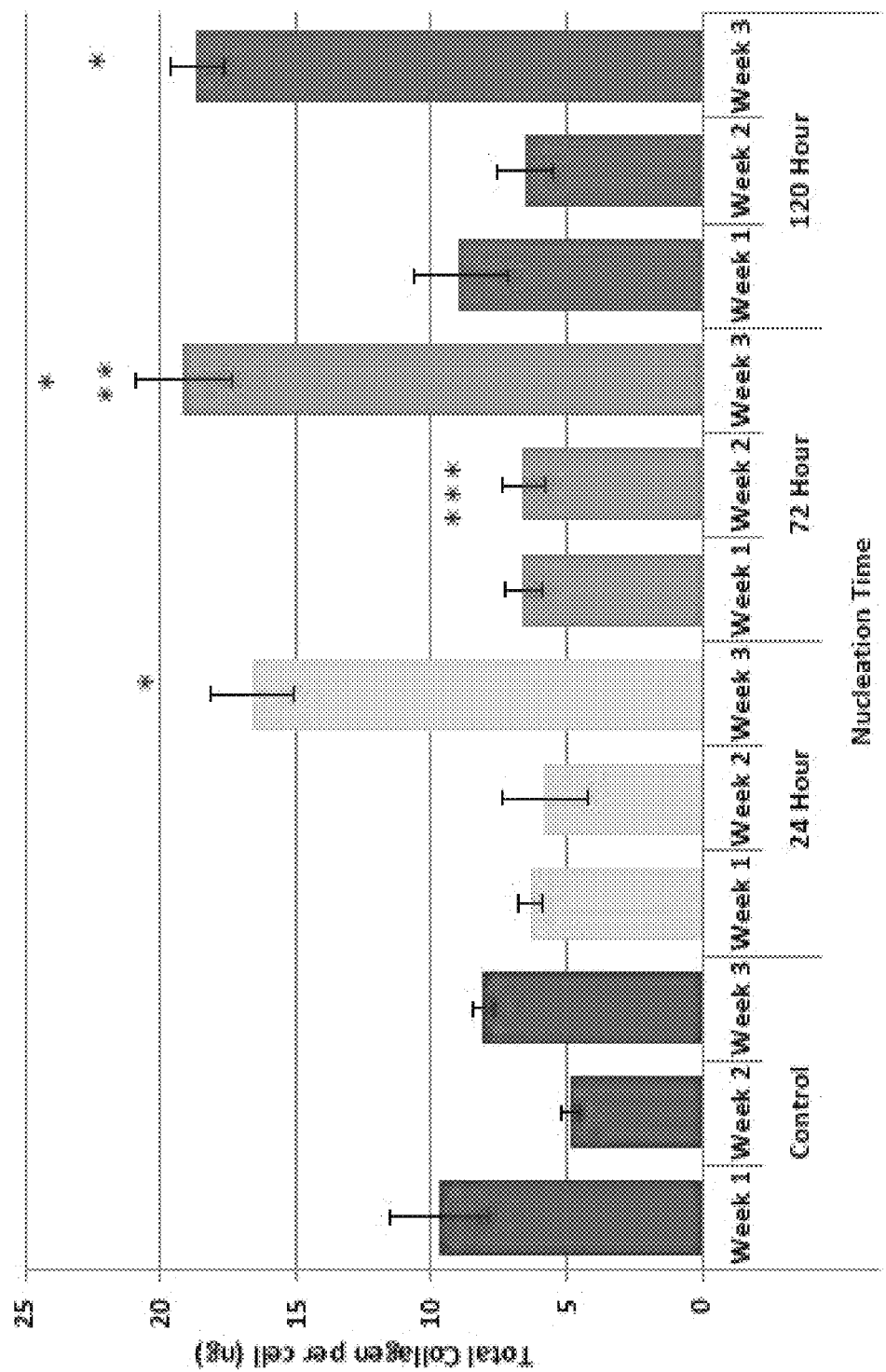
FIG. 13 depicts a graph of the total collagen synthesis in nanograms (ng) per cell of the control and nucleated 3D printed TPU scaffolds at a plurality of nucleation times after a first, second, and third week according to one or more aspects of the disclosure.

As shown in FIG. 13, extracellular collagen on nucleated 3D printed TPU scaffolds showed a greater than 100% increase in total collagen when compared to non-nucleated control after three weeks. Although no significant difference was observed after one week, 72 hour nucleated samples did show a 37% increase after two weeks.

Type I collagen was measured via type I collagen specific ELISA. Briefly, 100 µL of lysate was transferred to a 96-well plate pre-coated with rat immunoglobulin M antibody and incubated at room temperature for 2 hours. Aliquots were then decanted and the wells were washed to remove any unbound sample. A secondary type I collagen specific detection antibody was added to the well plate was incubated for an additional 2 hours followed by washing with buffer. Finally, streptavidin peroxidase was added to the plates resulting in a color reaction. An acidic stop solution was added to stop the reaction and the plate was read at 490 nm. Type I collagen was calculated based on a pre-made standard curve with known concentrations of type I collagen.

Figure 14:
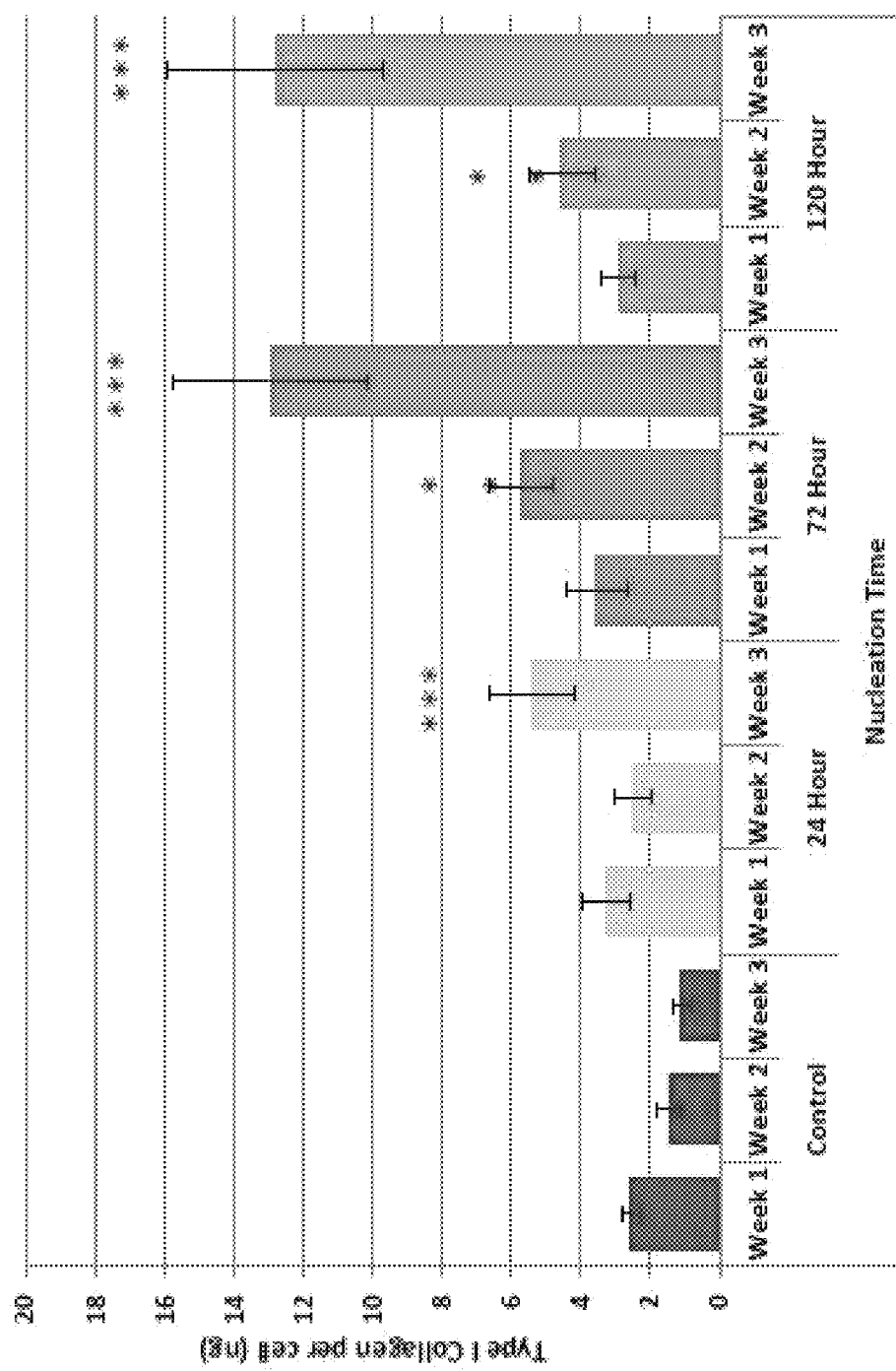
FIG. 14 depicts a graph of the total type I collagen deposition in nanograms (ng) per cell of the control and nucleated 3D printed TPU scaffolds at a plurality of nucleation times after a first, second, and third week according to one or more aspects of the disclosure.
Figure 15:
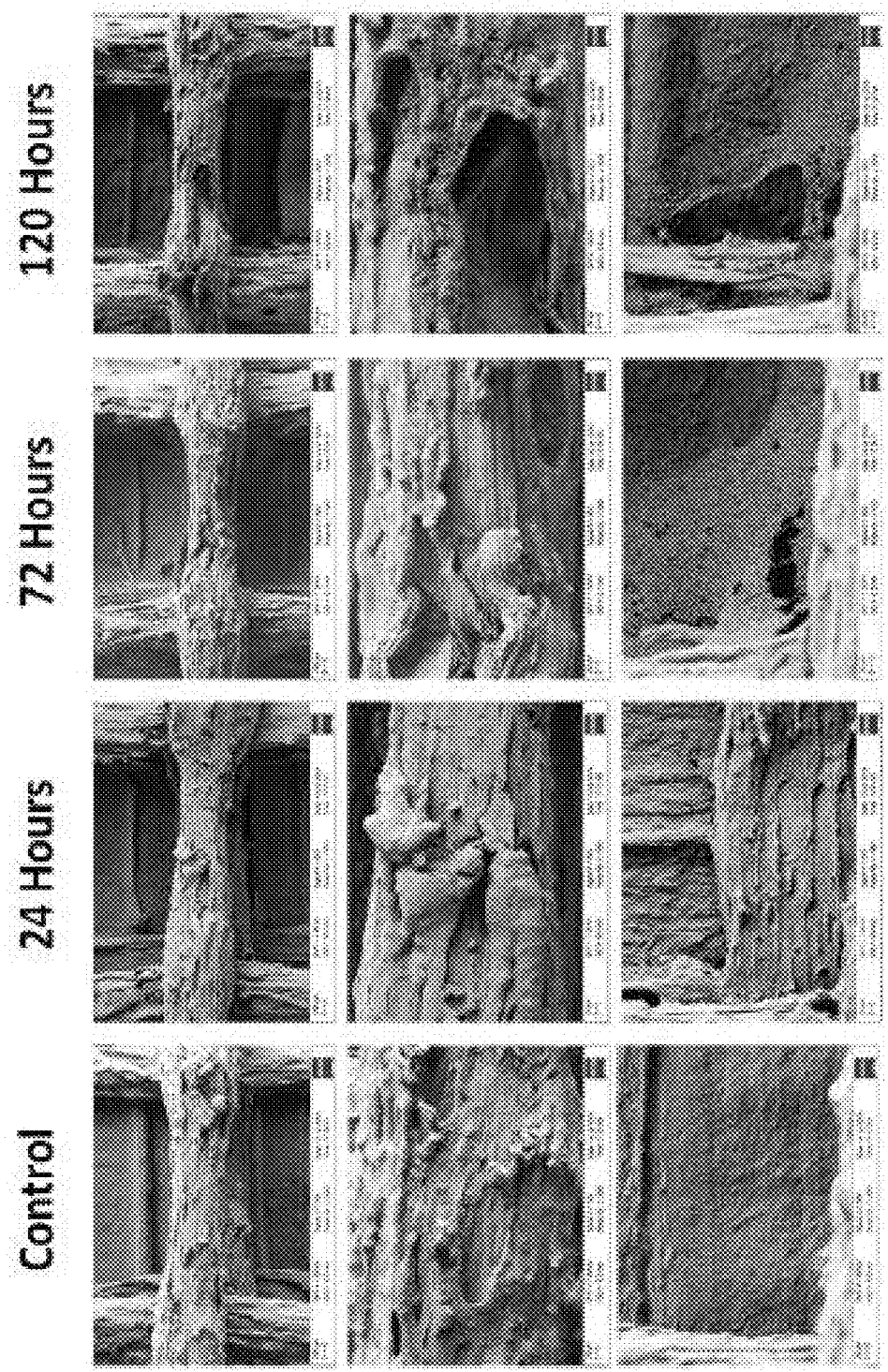
FIG. 15 depicts SEM images of the extracellular matrix deposition of the control and nucleated 3D printed TPU scaffolds at a plurality of nucleation times after two weeks according to one or more aspects of the disclosure.
Figure 17A:
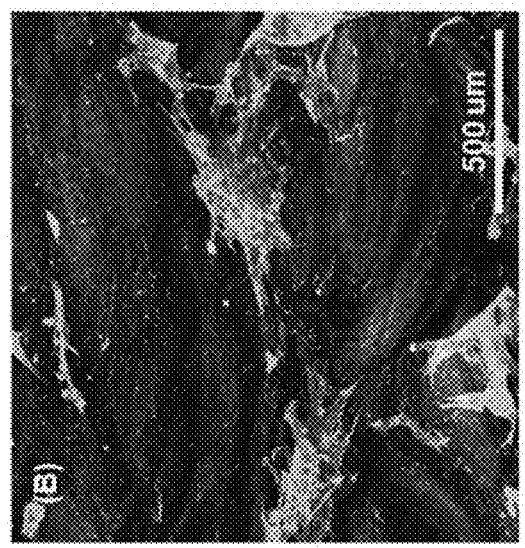
FIGS. 17A-17D depict confocal images of 3D printed TPU scaffolds cultured with mesenchymal stem cells (MSCs, FIGS. 17A, 17C) or a co-culture of MSCs and human umbilical vein endothelial cells (HUVECs, FIGS. 17B, 17D), stained for Osteopontin (dark staining) and von Willebrand factor (light staining) according to various embodiments of the disclosure.
Figure 17C:
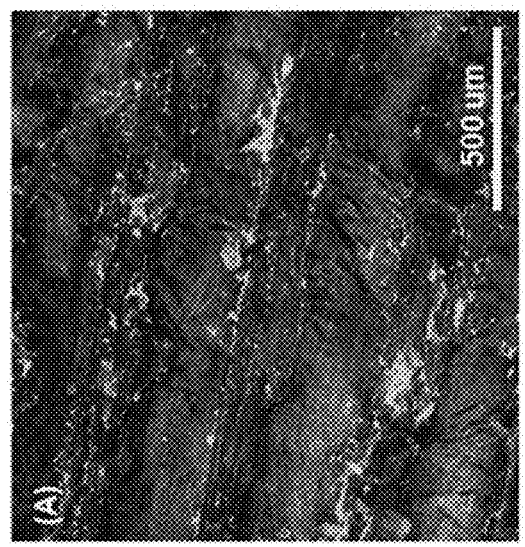
Figure 17B:
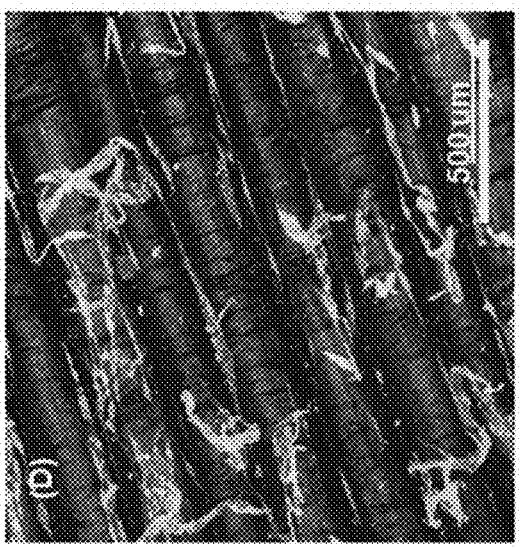
Figure 17D:

As shown in FIG. 14, 72 hour and 120 hour nucleated samples resulted in a 290% and 211% increase in type I collagen when compared to control after two weeks. In addition, all nucleated samples showed a significant increase when compared to non-nucleated control after three weeks. 24 hour nucleation yielded a near 4-fold increase with 72 hour and 120 hour nucleation resulting in an 11-fold increase, respectively. Furthermore, as shown in FIG. 15, SEM analysis of two-week differentiation illustrated the clear formation of extracellular matrix deposits which are most evident after 72 and 120 hour nucleation. Distinct collagen-like fibrous structures are visible with mineralized nodule formation.

All data presented are in the form of mean value±standard error of the mean. Student's t-test was used to determine significant differences amongst the groups with statistical significance considered at p<0.05. The scope of the work has great significance in the realm of 3D printed implantable bioactive polymeric scaffolds where a dearth of 3D printable cytocompatible material exists for use in bone tissue regeneration.

Example 3

Repair of Full Thickness Osteochondral Lesions Using 3D Printed, Nano-Porous Thermoplastic Polyurethane Implants in a Rodent Model Introduction Repair of full thickness cartilage and early stage osteochondral lesions has been a clinical challenge. Osteochondral scaffolds serve the purpose of providing a complex structure, often comprised of different patterns and/or different materials to stimulate bone and cartilage tissue ingrowth and development similar to the native articular tissue. The osteochondral region is characterized by the subchondral bone, a highly calcified and well aligned transitional region and the articulate cartilage. Research has focused on strategies that can either replicate the material composition or the structure of this region. The use of 3D printing holds great potential because it can easily modulate the internal structure of a scaffold from zone to zone, but there is a lack of viable material. Particularly, balance between biological response and manufacturing feasibility is paramount for clinical translation, and has been seldom explored for artificial regenerative osteochondral tissue.

There is a significant clinical need to treat young and active patients with cartilage lesions that are "critically sized" but are still not much larger than 1 cm without injuries in the subchondral bone. This represents a significant patient population (est. 1 million cases annually) which means that any implants for this population would need to be relatively small and produced in mass. For a 3D printing application, this means that production requires a highly economical scale, reliable accuracy and off-the-shelf availabilities when it comes to shipping, storing and handling. Thus, the exploitation of an acellular cartilage implant without any biologics that can be manufactured, sterilized and packaged is highly desirable for clinical translation.

To these ends, this project combined the advantages of 3D printing and nanoporous thermoplastic polyurethane (TPU) to repair full thickness osteochondral lesions and demonstrated its potential in a rodent model. The results show that this material allows for vascularized bone formation and has mechanical properties that are conducive to cartilage regeneration. On the translational side, TPU is entirely synthetic and can be easily manufactured using thermal processing and UV crosslinking methods. Structures used in this project were designed to promote efficient native cartilage, bone and vascular in-growth in appropriate and specified locations, and to have favorable mechanical and angiogenic properties. These features allow the synthetic, 3D printed implant to both support mechanical loading similar to native bone and cartilage, and to promote rapid and efficient fluid perfusion (e.g., arterial blood) throughout the implant, which is critical for the initial induction of progenitor cells and early vascular formation deep within the implant microarchitecture.

Materials and Methods

Methods for processing, design and printing were used, and the work presented here sought to translate initial in vitro study into a more clinically relevant in vitro and in vivo model, to evaluate complex tissue repair. A flow chart of the experimental design can be seen in FIG. 16A.

Scaffold Design and 3D Printing

Figure 18A:
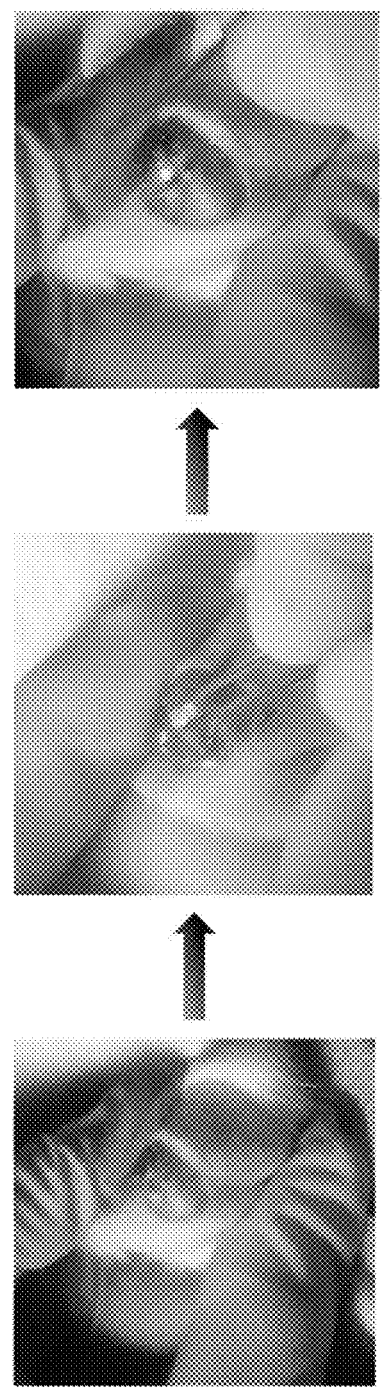
FIG. 18A depicts a method of making osteochondral defects in 6-week old female Sprague-Dawley rats using a lateral parapatellar approach according to various embodiments of the disclosure.
Figure 18B:
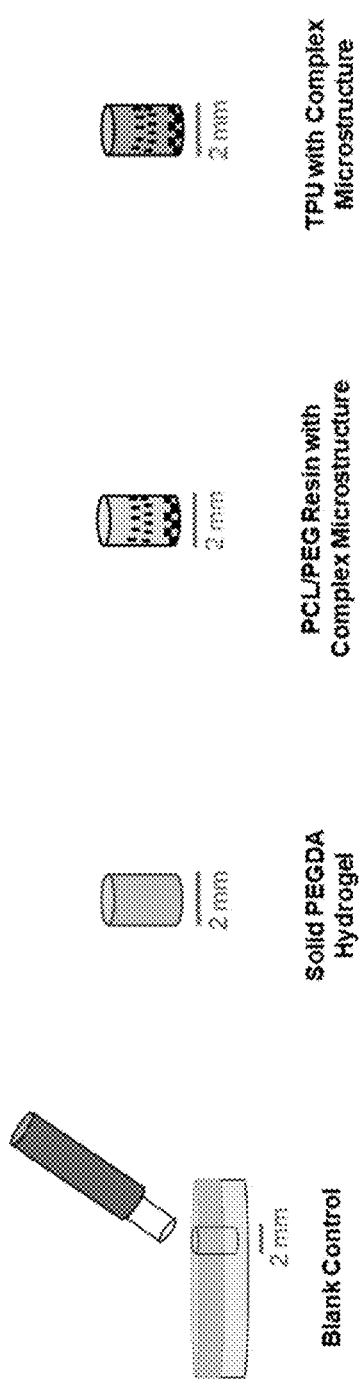
FIG. 18B depicts various designs of osteochondral implants that were press-fitted into the osteochondral defect according to various embodiments of the disclosure.

The novelty of the osteochondral implant stems from both its series in diverse micro-geometric porous structures within its internal architecture and its incorporation of TPU material. These structures have been designed to promote efficient native cartilage, bone, and vascular ingrowth in appropriate and specified locations, and to have favorable mechanical and blood flow properties. More specifically, the large pores found in the upper region of the implant's structure (FIG. 16B) combine to form microchannels that allow for enhanced blood flow properties. Rapid and fully penetrating supplies of blood and nutrients is key for both the recruitment and growth of autologous cells in situ. In the middle zone of the implant, the nanoporous structure not only mechanically mimics porous cartilage, but also has been shown to be advantageous for stem cell recruitment, growth, and differentiation. The lower region of the implant, labeled as the articulating surface, allows for a smooth transition to the nearby native tibia. Scaffolds were printed on both an Envision-TEC Bioplotter, as well as a tabletop Solidoodle fused deposition modeling (FDM) machine. For in vitro experimentation, scaffolds were designed in Rhinoscerous (Rhino) as 5 mm diameter disks with a 0.5 mm thickness. In vivo samples were also designed in Rhino as 2 mm diameter, 3 mm high cylinders. For all samples, scaffolds had a 250 µm feature size and layer thickness, with a 150 µm pore width and/or channel diameter. All models were exported as STL files and processed into GCODE files using Sli3r, or using Envision-TEC's proprietary software. Three main scaffold groups were printed for the in vivo study, a positive control of polyethylene diacrylate (PEGDA); an experimental composite of polyethylene glycol (PEG), nano hydroxyapatite (nHA) and polycaprolactone (PCL); and the TPU (FIG. 18B). The positive control and the experimental composite were prepared with a UV initiated photocrosslinker. The control was cast in a petri dish as a 3 mm deep layer and exposed to high intensity UV light for 15 minutes. The composite was printed on the Envision-TEC using a UV curing tool and protocol. TPU scaffold for both experiments were printed on the Solidoodle tabletop printer.

Co-Culture of HUVECs and MSCs

In vitro testing was performed using mesenchymal stem cells (MSCs, gifts from Dr. Patrick Hanley, Children's National Health System) and Human Umbilical Vein Endothelial Cells (HUVECs, Thermo Fisher Scientific). TPU samples were sterilized by exposure to UV light for 30 minutes and then washed with 70% ethanol. Samples were pre-wetted for 24 hours in a mixture of 1:1 complete cell media (CCM) and Medium 200 containing 10% low serum growth supplement (LSGS). TPU samples were then seeded with 100,000 MSCs and/or 100,000 HUVECs, and cultured in the same mix of CCM:LSGS. Samples were fixed in 10% formalin for 15 mins, permeabilized with 0.1% Triton X-100 for 10 mins. The fixed and permeabilized samples were kept frozen at −20° C. until staining.

Immunofluorescent Staining

Fixed and permeabilized cell-laden samples were blocked in 10% BSA for 30 mins. The cells were incubated with primary antibodies at 4° C. overnight. The following primary antibodies were used for staining: goat polyclonal anti-vWF antibodies (Santa Cruz Biotechnology) and mouse monoclonal anti-OPN antibodies (Santa Cruz Biotechnology). After incubation with primary antibodies, donkey anti-goat IgG-FITC (Santa Cruz Biotechnology) and chicken anti-mouse IgG-TR (Santa Cruz Biotechnology) as secondary antibodies were added and incubated 1 h, respectively. Samples were finally imaged on an Olympus confocal microscope.

Animal Studies

An osteochondral defect was created in the trochlear groove of the left knee of 68 6-week old female Sprague-Dawley rats. A lateral parapatellar approach to the knee was used and the defect was created with a 2.5 mm Kirschner wire (FIG. 18A). Four experimental groups included a blank control, a solid hydrogel implant, and two experimental implants (FIG. 18B). All samples were sterilized using a Sterrad XT low temperature plasma sterilizer. The osteochondral defect was created and then immediately repaired by press-fitting the experimental implant into the defect. At 1 and 3 months, samples were harvested and analyzed. The surgical procedure was successful in all animals and all subjects survived the follow-up time points.

In Vivo Sample Testing

For in vivo testing, samples harvested from rats (post 1 and 3 months) were processed in Fromacal to remove calcium from the tissue. Samples were then embedded in paraffin, sectioned on a microtome sectioning machine, and stained for hematoxylin and eosin. Samples were then viewed on a light microscope and photographed using a Nikon digital dual feed camera mounted on the microscope. Samples extracted at 3 months were also tested for glycosaminoglycan, collagen type I, and collagen type II content. A glycosaminoglycan detection kit (Blyscan) was used to test the samples for glycosaminoglycan matrix deposition. Samples were first digested via a papain digestion protocol consisting of soaking the sample in a papain extraction reagent (consisting of 400 mg sodium acetate, 200 mg EDTA, and 40 mg of cysteine hydrochloric acid) overnight in a 55° C. oven. Samples were then centrifuged at 10,000 g for 10 mins, where 50 µl of the supernatant was diluted with 50 µl of distilled water, transferred to a 96 well plate and reacted with a dye reagent. Once the reaction was complete, 200 µl of the sample were read on a photometric plate reader at a detection wavelength of 656 nm. Collagen type I and type II ELISA immunochemistry assays (Chondrex) were used to measure collagen type I and type II content. For these assays, samples were first digested via a pepsin digestion protocol consisting of soaking the samples in a solution of 0.1 mg/mL pepsin and 0.05 M acetic acid, vigorous mixing for 10 minutes, and placed on a shaker in 4° C. for 48 hours. Samples were centrifuged for 3 minutes at 10,000 rpm and its supernatant collected. Leftover pieces of the sample were further digested via elastase digestion, where a solution of 0.1 mg/mL of pancreatic elastase, 0.1M Tris base, and 0.15 M sodium chloride were added to the samples and mixed in a rotator at 4° C. overnight. This supernatant was collected and combined with the previous sample supernatant. For collagen type I ELISA, 100 µl of the digestion supernatant from each sample were transferred to a 96 well plate coated with capture antibodies, incubated at room temperature for 2 hours, and washed. Detection antibody solution was then added to each well, incubated at room temperature for 2 hours, subsequently washed, and a solution of streptavidin peroxidase was added. After another wash and the addition of an o-phenylenediamine dihydrochloride solution, the plate was read at 490 nm on a photometric plate reader. Collagen type II ELISA followed a similar protocol, where 200 µl of the digested supernatant of each sample was tested.

Results

Previous work demonstrated 3D printed TPU scaffolds yield dense 3D calcified ECM. However, vascularized bone tissue formation is critical for the successful grafting and integration of an orthopedic implant. Even in the case of a cartilage-focused replacement such as the 3D printed TPU presented in this work, the new cartilage and the replacement need to graft adequately to the subchondral bone. To this end, this project explored the angiogenic potential of TPU which has bioactive and mechanical properties conducive to cartilage regeneration. These 3D TPU constructs are entirely synthetic and can be easily manufactured using thermal processing and UV crosslinking methods.

An in vitro study was performed to evaluate vascularized bone formation (FIGS. 17A-17D). Samples cultured with MSCs alone, after 5 and 10 days, showed dense bone formation shown by osteopontin staining (dark staining) and some limited vascular activity without complex network formation. The co-culture groups with MSCs and HUVECs, which is more indicative of the in vivo environment upon implantation to a potential osteochondral defect site, demonstrated dense bone formation (dark staining) and excellent vascular cell activity after 5 days, and the formation of organized micro-vessels resembling vascular structures within osteons after 10 days (light staining). Interestingly, after 10 days, the osteopontin expressions conformed and resembled the 3D printed microstructure. In addition, the co-cultured scaffolds transverse vascular networks formed along 3D printed channels and were connected by perpendicular, shorter vessels, similar to native bone. These results show that in a more biomimetic co-cultured environment, our 3D printed TPU enables bone regeneration with formation of complex micro-vasculature, events that can be expected in situ upon implantation.

Figure 19:
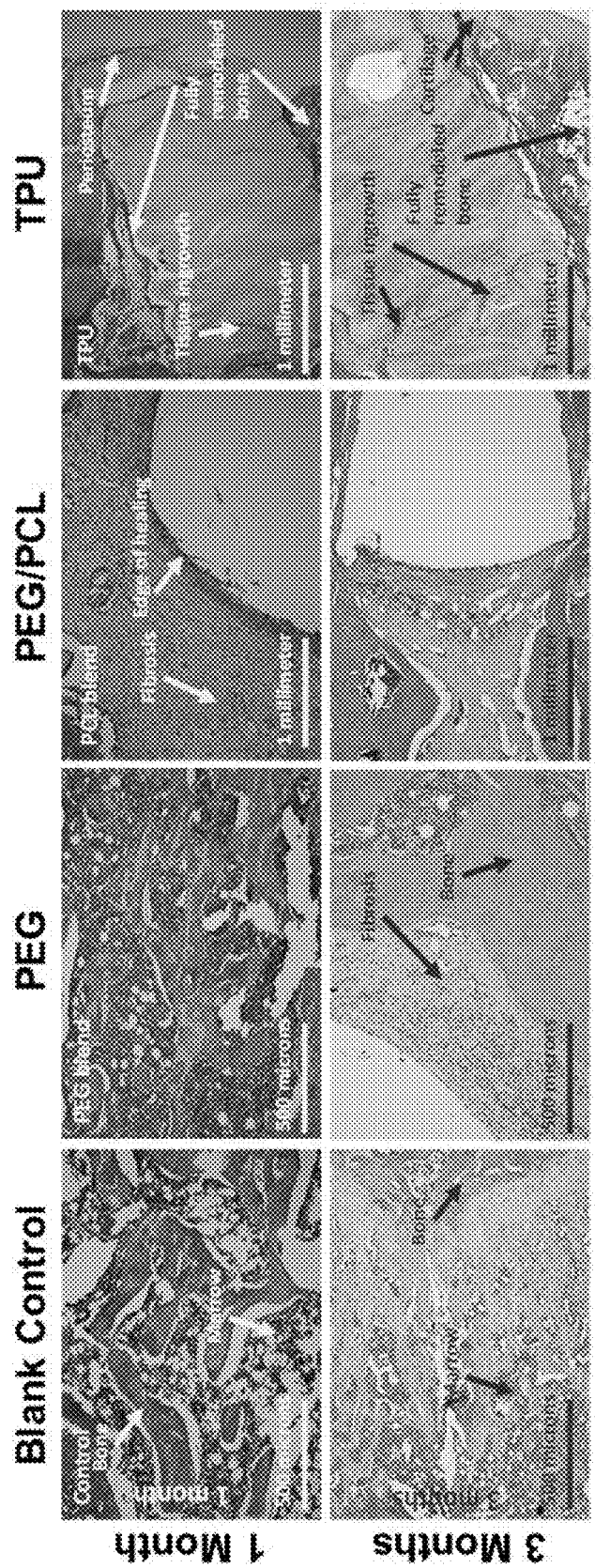
FIG. 19 depicts histology of tissue samples taken from rat osteochondral lesions harvested after 1 month (top panels) and 3 months (bottom panels) of healing according to various embodiments of the disclosure.
Figure 21A:
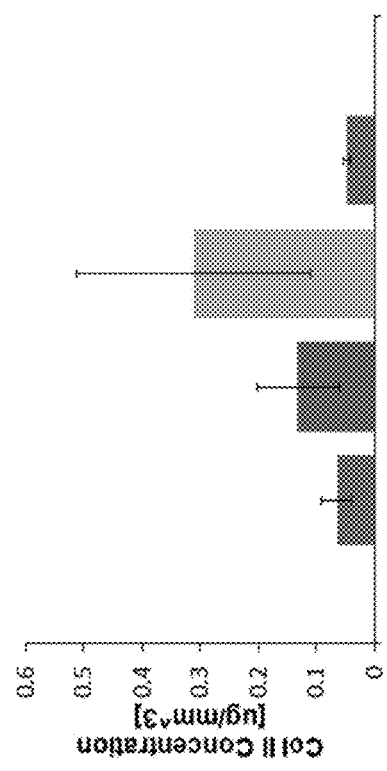
FIG. 21A depicts collagen I content extracted from osteochondral implants according to various embodiments of the disclosure.
Figure 21B:
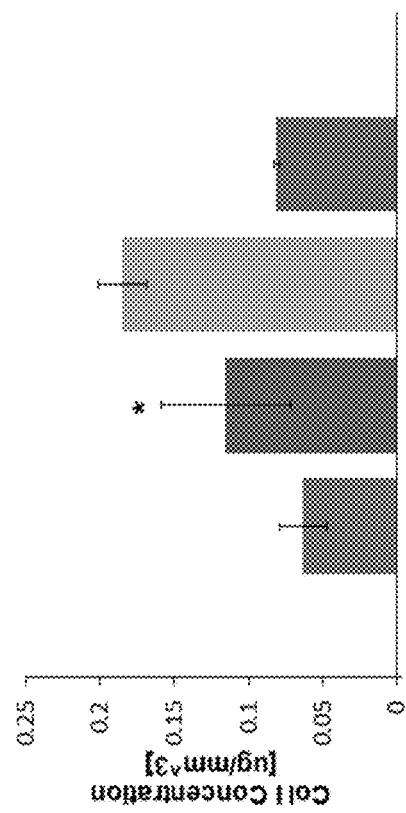
FIG. 21B depicts collagen II content extracted from osteochondral implants according to various embodiments of the disclosure.
Figure 21C:
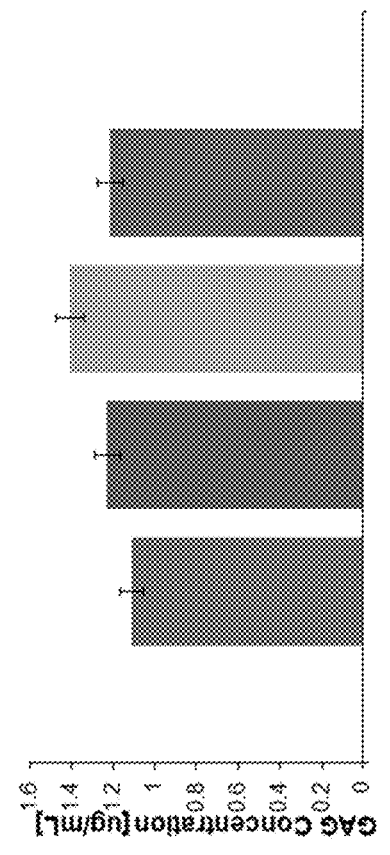
FIG. 21C depicts glycosaminoglycan (GAG) content extracted from osteochondral implants according to various embodiments of the disclosure.

Once it was established that TPU enables dense bone formation and neovascularization, the 3D printed TPU scaffolds were implanted in a rodent model. As demonstrated in FIG. 18A, a defect was created and inserted with implants of various groups. These groups included no treatments, solid PEGDA, PCL/PEG with complex microstructure and finally TPU with complex microstructures. After 1 month and 3 months, implants were extracted and stained with H&E. At 1 month, histologic analysis (FIG. 19) demonstrated limited bone remodeling and mostly formation of trabecular bone and marrow in the control and in the PEG group. The PCL based experimental implant showed the formation of extensive disorganized fibrosis around the implant with modest bone remodeling. On the other hand, TPU based material showed the formation of fully remodeled bone around the implant, and some bone invading the implant microstructure ("Tissue ingrowth", FIG. 19). At 3 months there were significant morphological changes to the tissue surrounding all implants. The control showed further marrow and trabecular bone. The PEG samples showed the continued formation of inflammatory fibrosis, and cystic activity on some samples. The PCL scaffold showed the formation of dense, disorganized non-inflammatory fibrocartilage. Most encouraging was the TPU implant which yielded the formation of new highly organized fibrocartilage fusing the implant to existing articulate cartilage. There was also the observation of blood vessel-like lumens within the present implant microstructures (FIGS. 20A-20C). Next, extracted implants after 3 months of post-implantation were also subject to additional analysis to test for collagen I, collagen II, and GAG concentrations (FIGS. 21A-21C). TPU had the highest levels of collagen I protein expression compared to the rest of the experimental groups, a sign for bone dense formation. In addition, TPU had the highest level of collagen II which indicated articular and/or hyaline cartilage formation. This was particularly exciting because it has been challenging for the field to develop a method to regenerate cartilages appropriate for joint surfaces. However, it should be noted that Collagen II expression on the TPU scaffolds was not statistically significant, so even though the TPU scaffold may support hyaline cartilage, it is not necessarily more effective at regenerating it. Moreover, TPU leads to increased GAG production which again is an indication for osteochondral tissue regeneration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A three-dimensional tissue scaffold comprising:
   (a) a first region comprising two or more layers of a first material and having a plurality of first pores, each having a first average pore width; and
   (b) a second region comprising two or more layers of a second material and having a plurality of second pores, each having a second average pore width,
   wherein a surface of the two or more layers of the first material, a surface of the two or more layers of the second material, or both, comprise a plurality of pits having an average width that is below the resolution of a rapid prototyping technology,
   wherein at least one of the first material and the second material is an insoluble component that remains after a soluble component of a composite material comprising the insoluble component and the soluble component is dissolved by a solvent, and
   wherein the plurality of pits on the surface of the two or more layers of the first material, the plurality of pits on the surface of the two or more layers of the second material, or both, correspond to an absence of the soluble component.

2. The three-dimensional tissue scaffold of claim 1, wherein the plurality of pits have an average width of about 200 nm to about 50 µm.

3. The three-dimensional tissue scaffold of claim 1, wherein the first average pore width and the second average pore width are the same.

4. The three-dimensional tissue scaffold of claim 1, wherein the first material and the second material are the same.

5. The three-dimensional tissue scaffold of claim 1, wherein the solvent is water.

6. The three-dimensional tissue scaffold of claim 1, wherein the insoluble component is selected from the group consisting of: thermoplastic polyurethane (TPU), polycaprolactone (PCL), poly co-glycolic acid (PLGA), polylactic acid (PLA), and high impact polystyrene (HIPS).

7. The three-dimensional tissue scaffold of claim 1, wherein the soluble component is selected from the group consisting of: polyvinyl alcohol (PVA), salt, sugar or sugar glass, polyethylene glycol (PEG) or any uncrosslinked functionalized derivative thereof, gelatin or any derivative thereof, poly co-glycolic acid (PLGA), alginate, and sodium bicarbonate.

8. The three-dimensional tissue scaffold of claim 1, wherein the composite material comprises from about 50 wt % insoluble component to about 95 wt % insoluble component.

9. The three-dimensional tissue scaffold of claim 1, wherein the composite material comprises from about 5 wt % soluble component to about 50 wt % soluble component.

10. The three-dimensional tissue scaffold of claim 1, wherein the first average pore width is from about 100 µm to about 200 µm.

11. The three-dimensional tissue scaffold of claim 1, wherein the second average pore width is from about 500 µm to about 1 mm.

12. The three-dimensional tissue scaffold of claim 1, wherein the two or more layers of the first material are printed in a first geometric pattern, and the two or more layers of the second material are printed in a second geometric pattern.

13. The three-dimensional tissue scaffold of claim 12, wherein the first geometric pattern and the second geometric pattern are the same.

14. A method of manufacturing a three-dimensional tissue scaffold, wherein the three-dimensional tissue scaffold comprises:
   a first region comprising two or more layers of a first material and having a plurality of first pores, each having a first average pore width; and
   a second region comprising two or more layers of a second material and having a plurality of second pores, each having a second average pore width;
   wherein a surface of the two or more layers of the first material, a surface of the two or more layers of the second material, or both, comprise a plurality of pits having an average width that is below the resolution of a rapid prototyping technology,
   the method comprising:
   (a) fabricating the first region by printing two or more layers of the first material comprising the plurality of first pores;
   (b) fabricating the second region by printing two or more layers of the second material comprising the plurality of second pores,
   wherein at least one of the first material and the second material comprises a composite material having an insoluble component and a soluble component; and
   (c) dissolving the soluble component from the composite material, thereby manufacturing the three-dimensional tissue scaffold,
   wherein, after the dissolving of (c), the three-dimensional tissue scaffold comprises a plurality of pits along a surface of the insoluble component, wherein the plurality of pits comprise an average width that is below the resolution of a rapid prototyping technology.

15. The method of claim 14, wherein the plurality of pits comprises an average width of about 200 nm to about 50 µm.

16. The method of claim 14, wherein the fabricating of (a), (b), or both comprises printing the two or more layers using one or more rapid prototyping technologies selected from the group consisting of: stereolithography, digital light processing, fused deposition modeling, selective laser sintering, selective laser melting, electron beam melting, laminated object manufacturing, bio-plotting, and deposition printing.

17. The three-dimensional tissue scaffold of claim 1, wherein the insoluble component is thermoplastic polyurethane (TPU).

18. The three-dimensional tissue scaffold of claim 1, wherein the soluble component is polyvinyl alcohol (PVA).

\* \* \* \* \*